United States Patent
Cohen et al.

(10) Patent No.: US 7,148,478 B2
(45) Date of Patent: Dec. 12, 2006

(54) ELECTRICAL MEASUREMENTS IN SAMPLES

(75) Inventors: Hagai Cohen, Rehovot (IL); Igor Lubomirsky, Petach Tikva (IL)

(73) Assignee: Yeda Research and Development Company Ltd., Rehovot (IL)

( * ) Notice: Subject to any disclaimer, the term of this patent is extended or adjusted under 35 U.S.C. 154(b) by 159 days.

(21) Appl. No.: 10/987,192

(22) Filed: Nov. 15, 2004

(65) Prior Publication Data

US 2006/0103395 A1    May 18, 2006

Related U.S. Application Data

(63) Continuation-in-part of application No. PCT/IL04/000963, filed on Oct. 21, 2004.

(60) Provisional application No. 60/512,784, filed on Oct. 21, 2003.

(51) Int. Cl.
*H01J 37/26* (2006.01)
*G01R 31/305* (2006.01)

(52) U.S. Cl. ........... 250/306; 250/307; 250/492.2; 250/492.3

(58) Field of Classification Search ............ None
See application file for complete search history.

(56) References Cited

U.S. PATENT DOCUMENTS

| | | | |
|---|---|---|---|
| 6,720,556 B1 * | 4/2004 | Cohen et al. ............... | 250/306 |
| 6,774,363 B1 | 8/2004 | Fukuda et al. | |
| 2002/0020814 A1 | 2/2002 | Cohen et al. | |

OTHER PUBLICATIONS

Doron-Mor, I., et al., "Controlled surface charging as a depth-profiling probe for mesoscopic layers", *Nature*, vol. 406, pp. 382-385, (2000).

Shabtai, K., et al., "High-Resolution Lateral Differentiation Using a Macroscopic Probe: XPS of Organic Monolayers on Composite Au-$SiO_2$ Surfaces", *J. Am. Chem. Soc.*, vol. 122, pp. 4959-4962, (2000).

Barr, T.L., "Studies in differential charging", *J. Vac. Sci. Technol. A.*, vol. 7, No. 3, pp. 1677-1683, (1989).

Lau, W.M., "Use of surface charging in x-ray photoelectron spectroscopic studies of ultrathin dielectric films on semiconductors", *Appl. Phys. Lett.*, vol. 54, No. 4, pp. 338-340, (1989).

(Continued)

*Primary Examiner*—Nikita Wells
(74) *Attorney, Agent, or Firm*—Nath & Associates PLLC; Gregory B. Kang; Derek Richmond

(57) ABSTRACT

A method and device are presented for measuring the electrical properties of a specimen. The specimen is excited with high energy radiation to cause emission of internal charged particles from the specimen. Electrical power is supplied to a circuit, that is formed by the specimen and any added component connected to a back contact of the specimen. The electric power supply includes at least one of the following: irradiating the circuit with low energy charged particles; subjecting the circuit to an external field of the kind affecting the flux of emitted internal charged particles, and supplying a bias voltage to the back contact of the specimen. During the power supply to the specimen, at least one of the following is carried out: an electric current through the specimen is measured, and the emitted charged particles are analyzed versus their energy (using a contact-less voltmeter) which provides local potential values at chemical entities of the specimen. This technique enables determination of rich, chemically resolved, electrical properties of a specimen, such as I–V characteristic, and/or evaluation of a work function characteristic, and/or characterization of electric leakage or breakdown conditions of the sample, and/or characterization of accumulation of charge within at least one region of the sample, and/or chemically resolved photovoltaic characteristics (photovoltage and/or photocurrent) of the sample.

75 Claims, 16 Drawing Sheets

OTHER PUBLICATIONS

Lau, M.W., et al., "Measurements of interface state density by X-ray photoelectron spectroscopy", *Surface Science*, vol. 245, pp. 345-352, (1991).

Chan, R.W.M., et al., "Modified surface charge spectroscopy for the characterization of insulator/semiconductor structures", *J. Appl. Phys.*, vol. 49, No. 7, pp. 3635-3639, (1996).

Caron, L.G., et al., "Electron transmission in the energy gap of thin films of argon, nitrogen, and *n*-hexane", *Phys. Rev. B*, vol. 33, No. 5, pp. 3027-3038, (1986).

Miller, J.D., et al., "Composite Interface Analysis using Voltage Contrast XPS", *Zajac, Surf. Interf. Anal.*, vol. 20, pp. 977-983, (1993).

\* cited by examiner

ELECTRICAL MEASUREMENTS IN SAMPLES

This is a Continuation-In-Part of International Patent Application PCT/IL2004/000963 with an international filing date of 21 Oct. 2004 and claims benefit of U.S. Provisional Patent Application 60/512,784 filed on 21 Oct. 2003, the contents of which are hereby incorporated by reference in their entirety.

FIELD OF THE INVENTION

This invention is generally in the field of measurement/inspection techniques and relates to a method and system for electrical measurements in samples.

RELATED ART

The following publications are considered to be pertinent for the purpose of understanding the background of the present invention:
1. I. Doron-Mor, A. Hatzor, A. Vaskevich, T. van der Boom-Moav, A. Shanzer, I. Rubinstein and H. Cohen, *Controlled surface charging as a depth-profiling probe for mesoscopic layers*, Nature 406, 382 (2000);
2. K. Shabtai, I. Rubinstein, S. R. Cohen and H. Cohen, *J. Am. Chem. Soc.* 122, 4959–4962 (2000);
3. J. D. Miller, W. C. Harris and G. W. Zajac, *Surf. Interf. Anal.* 20, 977 (1993);
4. T. L. Barr, *J. Vac. Sci. Technol. A* 7, 1677 (1989);
5. W. M. Lau, *Appl. Phys. Lett.* 54, 338 (1989);
6. W. M. Lau and X. W. Wu, *Surf. Sci.* 245, 345 (1991);
7. R. W. M. Chan, R. W. M. Kwok and W. M. Lau, *J. Appl. Phys.* 79, 3635 (1996);
8. Caron, L. G, Perluzzo, G, Bader, G & Sanche, L. Electron transmission in the energy gap of thin films of argon, nitrogen, and n-hexane. *Phys. Rev. B* 33, 3027–3038 (1986).

BACKGROUND OF THE INVENTION

Electronic systems generally include test points on which the performance of selected sections can be characterized. The need in such tests grows with the complexity of the system. Small (nanoscale, and in particular molecular level) devices, especially complex heterostructures grown as a single component, raise demanding requirements on the electrical measurements in these devices.

The existing electrical measuring tools, typically utilizing an electrodes' arrangement, cannot probe selectively the inner regions of such structures. These tools typically detect an integral signal, associated with a spatial region in between two (or more) attached electrodes. This fact limits the (electrical) resolution both vertically and laterally. Therefore, even the finest solid-state electrodes are practically incapable of measuring at the sub-molecular scale. The existing developments in this technical field thus present a principal problem in both accessing the inner components of a structure under electrical measurements, and in achieving enhanced spatial (electrical) resolution.

The electric contact to a given surface is frequently a serious problem by itself, introducing a new unknown interface with unknown electric properties. In various recently developed systems, which consist of fine structural variations close to the very surface, an attached contact may even affect the system directly. This difficulty can be answered efficiently by non-contact tools.

Recently, a new method for non-damaging depth profiling in the 15 nm range has been demonstrated [1]. This method is based on controlled surface charging (CSC) [1,2] in X-ray photoelectron spectroscopy (XPS). XPS is a powerful surface analytical tool, providing superior information on the chemical composition of surfaces and interfacial layers. The technique is based on illumination of the surface with X-rays and analysis of the photoelectrons ejected from the surface, thereby determining the identity and chemical state of atoms located on the surface and up to about 15 nm deep. In contrast to its nanometer-scale depth sensitivity, in the lateral direction XPS is essentially a macroscopic technique.

In the above-indicated method, as well as some other related techniques [3–5], the XPS line shifts, occurring upon charging, are used in order to extract position of atoms. Several works aimed at extracting qualitatively electrical aspects out of differential charging effects have been presented [6, 7].

U.S. 20020020814, assigned to the assignee of the present application, discloses an electron spectroscopy employing controlled surface charging. According to this technique, a sample is examined by performing a first spectroscopic analysis of a surface portion of the sample when the sample surface portion is in a first electrical charge state, placing the sample surface portion in a second electrical charge state that is different from the first electrical charge state and performing a second spectroscopic analysis of the surface portion of the sample when the sample surface portion is in the second electrical charge state. By comparing the first spectroscopic analysis result with the second spectroscopic analysis result at least one of structural and electrical information about the sample can be obtained.

SUMMARY OF THE INVENTION

There is a need in the art to facilitate electrical measurements in various samples, especially small (e.g. nanoscale) and complex samples, by providing a novel measuring method and device capable of local probing (i.e., probing selectively different regions) of the sample, including internal regions thereof.

The technique of the present invention presents the so-called "chemically resolved electrical measurements" (CREM). The technique provides unique sensitivity to details in electrical response mechanisms. Additionally, it exhibits improved top contact performance and powerful in-situ analytical capabilities. Realizable with commonly available equipment for its constructional parts, the CREM system of the present invention is effective for a broad range of heterostructured systems, ranging from the nanoscale up to micrometer and larger scales.

The main idea of the present invention consists of utilizing non-wired currents, namely beams of charged particles (e.g., electrons), which allow direct access to inner, sub-surface regions of the sample under measurements. In other words, the present invention utilizes such charged particles' beams as unique electrodes. Energy filtering is used to achieve chemical selectivity or, alternatively, improved (sub-nanometer) spatial resolution.

The technique of the present invention is general, and utilizes such main functional parts as an excitation source (e.g., a monochromatic X-ray beam typically used in XPS) for ejecting internal charged particles (e.g., electrons) from the sample; a detection system that includes a charged particles' spectrometer (e.g., electron spectrometer) for analyzing the ejected charged particles vs their kinetic energy, and/or an ampermeter for measuring an electric current through the sample; an electric power supply system, which may include a source of low energy charged particles (e.g., an electron flood gun (eFG) or an ion beam source (e.g., $He^+$-beam), typically operating with low energy beams), or a source of external field affecting the amount of internal charged particles ejected by the excitation source, and may include a voltage supply unit for supplying a bias voltage to the back contact of the sample. The invention may also utilize an electronic device including one or more components, such as external resistors.

It should be noted that, generally, the excitation source can be any of the following: an electromagnetic radiation source (e.g. X-ray, UV, visible light), a high energy electron beam source or, in certain cases, even an ion beam source.

Preferably, the present invention takes advantages of electron spectroscopy, e.g. XPS or Auger electron spectroscopy (AES), and utilizes the property that the energy of an emitted electron directly correlates with the local potential at its initial site. Hence, such an electron can be used as an internal probe of potential. Moreover, the analytical capabilities of XPS and AES, resolving different chemical species, provide a powerful net on which the electrical information can be projected. The method is similarly applicable with other charged particle spectroscopies.

According to the technique of the present invention, a charged particles' spectrometer (analyzer) is operated as a unique multi-channel voltmeter within a circuit, which includes non-wired (beam) currents, namely charged particles (electrons) traveling along macroscopic paths in the vacuum. According to the present invention, a generalized circuitry is established adding such a non-contact component as a power supply based on a beam of charged particles, the so-called "soft electrons", which are low-energy or slow electrons (generally "charged particles"). In this connection, it should be understood that this low energy varies from application to application. Typically these low-energy or slow electrons are a few eV in kinetic energy, up to 10 eV. In measurements of the I–V characteristic of a sample, this usually corresponds to 0–5 eV, but it can be higher in specific cases. In the work-function measurements, the energy is in a range of 0–10 eV (usually 0–4 eV). In photovoltaic measurements, like in the I–V measurements, the range of 0–5 eV is reasonable. In the electrical breakdown studies, the practically interesting range is still 0–5 eV, but one can go far above and still get interesting information. Generally, the low-energy electrons are electrons with up to about 20 eV energy, preferably, about 0–10 eV.

The technique of the present invention provides for deriving a spectrally resolved I–V curve of a self-assembled monolayer, free of substrate and top contact contributions, with no need for improved metallic substrates. In other words, the present invention provides for measuring in a sample on the nanoscale composed, for example, of several metals and dielectrics, or semiconductors, to obtain the I–V curve of each of these materials, selectively. This can be carried out for surface, as well as sub-surface components of the sample. The present invention offers unique capabilities in direct electrical analysis of internal selected regions, and can be used in various applications of semiconductor-based heterostructures, particularly in molecular electronics.

The present invention also provides chemically resolved photoresponse measurements (photovoltage and photocurrent) under external fields. To this end, an additional electromagnetic radiation source is applied as well to the sample under measurements.

The present invention also provides for work function (WF) evaluation. In this respect, the technique of the present invention is advantageously capable of mapping the WF. It can also differentiate between different (vertical and/or lateral) surface regions (i.e., the metal vs its oxide), and is technically easy and reliable.

Additionally, the technique of the present invention provides for electrical leakage or breakdown characterization through dielectric spacers in the sample. Failure analysis and more generally, characterization of electric stability across dielectric components, is an important issue in various devices. Usually, such studies, in particular the tests of electric breakdown or shortcuts across spacers, are based on current measurements under elevated fields, applied by external electrodes. This approach becomes quite limited with sub-micron samples, and certainly with nano-scale devices. At the sub-micron length scales, electrodes should become an integral part of the design, imposing new restrictions and limitations on the performance of the system. Moreover, even when integrated into the device, such electrodes probe large regions and hence are limited in finding the "weak point" of a system. Existing electrical tools do not provide for a flexible, yet selective access to regions buried within a heterostructure.

The technique of the present invention provides a new way to characterize electric breakdown processes across buried (shallow) regions. The method can easily identify the "weak point" and, in addition, allow unique characterization of the defected regions. It is based on the above-described way of measuring the local potential, using electron spectroscopy tools. The invented approach consists of applying chemically selective electrical measurements, such that fine selectivity of domains, including buried ones, can be achieved. External bias on the sample is added when elevated potential gradients are required at the breakdown condition. As indicated above, the "voltmeter" of the circuit is an electron spectrometer. In addition to the site selectivity it provides, it can give valuable information on the defected regions: their chemical characterization, effective resistance (at the breakdown channels), etc.

It should be noted that, generally, the breakdown analysis technique of the present invention is not limited to thin structures. It can be applied to macroscopically thick structures as well, in which case the electrical potential detection remains limited to surface regions only.

Moreover, the method of the present invention provides for distinguishing (via differential charging effects) between different electrical domains at the breakdown situation. In particular, the discharge channels within a macroscopic sample are resolvable by the present method. The analysis area in this technique can vary significantly. In certain applications, a macroscopic analysis area (e.g. 1 mm in diameter) becomes an important advantage, achieving, for example, fast quality analyses by reducing the needs in lateral scanning.

There is thus provided, according to one aspect of the present invention, a method for measuring the electrical properties of a sample, the method comprising:

(i) exciting the sample with high energy radiation to cause emission of internal charged particles from the sample;

(ii) supplying electrical power to a circuit formed by the sample and any added component connected to a back contact of the sample, said supplying of electric power comprising at least one of the following: irradiating the sample by low energy charged particles, subjecting the sample to an external field affecting the flux of emitted internal charged particles, and supplying a bias voltage to the back contact of the sample;

(iii) during the power supply to the sample, carrying out at least one of the following: measuring the emitted charged particles versus their energy, and measuring an electric current through the sample; thereby enabling determination of the electrical properties of the sample.

The measured spectral data (emitted charged particles versus their energy) is indicative of local potential values at different chemical entities of the sample.

The measured electrical properties include at least one of the following: spectrally resolved (e.g. chemically resolved) I–V characteristic of the sample; a work function characteristic of the sample; electric leakage or breakdown conditions of the sample; and accumulation of charge within at least one region of the sample.

For the I–V characteristic measurements, the electric power supply preferably includes irradiation of the sample by low energy charged particles. As for the application of the external field affecting the flux of emitted internal charged particles, and the bias voltage to the back contact of the sample, either one or both may also be used. Generally, the determination of the spectrum might be sufficient for these measurements, but preferably the electric current through the sample is also measured.

For the work function evaluation, the electric power supply includes irradiation of the sample by low energy charged particles; and may also include application of either one of the external field and the bias voltage or both of them. Measured data may include only the spectrum or both the spectrum and the electric current through the sample.

In order to determine electric leakage or breakdown conditions of the sample, the electric power supply preferably includes irradiation of the sample by low energy charged particles; and may also include application of either one of the external field and the bias voltage or both of them. The measured data includes the spectrum, and may also include the electric current through the sample.

For the accumulation of charge measurements, the electric power supply preferably includes irradiation of the sample by low energy charged particles; and may also include application of either one of the external field and the bias voltage or both of them. The measured data preferably includes the spectrum, and may also include the electric current through the sample.

As indicated above, the excitation source applied to the sample to cause emission of internal charged particles may include an X-ray gun, and/or at least one source of electromagnetic radiation and/or an electron gun and/or a gun bombarding the sample with ions or neutrals.

The charged particles of the electric power supply may include an electron beam (to thereby create a negative voltage supply to the sample), or an ion beam (for thereby creating a positive or negative voltage supply to the sample). The power supply can be operable in a DC or AC modes, as set in its control system.

The low-energy charged particles may be electrons or ions. The application of the external electrical field may for example be achieved by means of a grid-like electrode.

It should be understood that the terms "high energy" and "low energy" used herein are relative terms. The "high energy" radiation is such as to cause emission of internal charged particles from the sample, and the "low energy" of irradiating charges particles (e.g., up to 20 eV in kinetic energy, but usually up to 5 eV only) is aimed to apply electrical power to the sample, usually not causing emission of internal particles.

According to the invention, application of additional optical signals may also be provided. The two output signals, namely the sample current and the spectral information, as well as all input signals, X-ray, electrical power and optical illumination, are correlated in this analysis.

The analysis of the response of the sample (i.e., emitted charged particles) and/or an electric current through the sample and/or photovoltage or photocurrent of the sample is carried out by a detection system, which includes a distant charged particles' spectrometer (analyzer) and a detector connected to the output of the spectrometer; and/or an ampermeter. The spectrometer is not limited to any specific type of operation. It can be based, for example, on electrostatic tilting fields, on time-of-flight measurements, etc.

According to another aspect of the invention, there is provided a method for measuring the electrical properties of a sample, the method comprising:
  (i) exciting the sample with high energy radiation to cause emission of internal charged particles from the sample;
  (ii) supplying variable electrical power to a circuit formed by the sample and any added component connected to a back contact of the sample, said supplying of electric power comprising at least one of the following: irradiating the circuit by low energy charged particles, subjecting the circuit to an external field affecting the flux of emitted internal charged particles, and applying bias voltage to the back contact of the sample;
  (iii) during the variable power supply to the sample, measuring an electric current through the sample, and measuring the emitted charged particles versus their energy thereby extracting local potential values at chemical entities of the sample, thereby enabling determination of spectrally resolved I–V characteristic of the sample.

According to yet another aspect of the invention, there is provided a method for measuring the electrical properties of a sample, the method comprising:
  (i) exciting the sample with high energy radiation to cause emission of internal charged particles from the sample;
  (ii) supplying variable electrical power to a circuit formed by the sample and any added component connected to a back contact of the sample, said supplying of electric power comprising at least one of the following: irradiating the circuit by low energy charged particles, subjecting the circuit to an external field affecting the flux of emitted internal charged particles, and applying bias voltage to the back contact of the sample;
  (iii) during the variable power supply to the sample, measuring the emitted charged particles versus their energy thereby extracting local potential values at chemical entities of the sample, thereby enabling determination of spectrally resolved I–V characteristic of the sample.

According to yet another aspect of the invention, there is provided a method for measuring the electrical properties of a sample, the method comprising:
  (i) exciting the sample with high energy radiation to cause emission of internal charged particles from the sample;
  (ii) supplying electrical power to a circuit formed by the sample and any added component connected to a back contact of the sample, said supplying of electric power comprising irradiating the sample by low energy charged particles, and carrying out at least one of the following: supplying a bias voltage to the back contact of the sample, and subjecting the sample to an external field affecting the flux of emitted internal charged particles;
  (iii) during the electric power supply to the sample, measuring the emitted charged particles versus their energy, and thereby extracting local potential values at chemical entities of the sample and enabling evaluation of a work function characteristic of the sample.

According to yet another aspect of the invention, there is provided a method for measuring the electrical properties of a sample, the method comprising:
(i) exciting the sample with high energy radiation to cause emission of internal charged particles from the sample;
(ii) supplying electrical power to a circuit formed by the sample and any added component connected to a back contact of the sample, said supplying of electric power comprising irradiating the sample by low energy charged particles, and carrying out at least one of the following: supplying a bias voltage to the back contact of the sample, and subjecting the sample to an external field affecting the flux of emitted internal charged particles;
(iii) during the electric power supply to the sample, measuring an electric current through the sample and measuring the emitted charged particles versus their energy, and thereby extracting local potential values at chemical entities of the sample and enabling evaluation of a work function characteristic of the sample.

According to yet another aspect of the invention, there is provided a method for measuring the electrical properties of a sample, the method comprising:
(i) exciting the sample with high energy radiation to cause emission of internal charged particles from the sample;
(ii) supplying electrical power to a circuit formed by the sample and any added component connected to a back contact of the sample, said supplying of electric power comprising at least one of the following: irradiating the sample by low energy charged particles, applying bias voltage to the back contact of the sample, and subjecting the circuit to an external field affecting the flux of emitted internal charged particles;
(iii) during the electric power supply, measuring the emitted charged particles versus their energy thereby extracting local potential values at chemical entities of the sample, thereby enabling characterization of electric leakage or breakdown conditions of the sample.

According to yet another aspect of the invention, there is provided a method for measuring the electrical properties of a sample, the method comprising:
(i) exciting the sample with high energy radiation to cause emission of internal charged particles from the sample;
(ii) supplying electrical power to a circuit formed by the sample and any added component connected to a back contact of the sample, said supplying of electric power comprising irradiating the sample by low energy charged particles, and applying bias voltage to the back contact of the sample;
(iii) during the electric power supply, measuring the emitted charged particles versus their energy thereby extracting local potential values at chemical entities of the sample, thereby enabling characterization of electric leakage or breakdown conditions of the sample.

According to yet another aspect of the invention, there is provided a method for measuring the electrical properties of a sample, the method comprising:
(i) exciting the sample with high energy radiation to cause emission of internal charged particles from the sample;
(ii) supplying electrical power to a circuit formed by the sample and any added component connected to a back contact of the sample, said supplying of electric power comprising at least one of the following: irradiating the circuit by low energy charged particles, applying bias voltage to the back contact of the sample, and subjecting the circuit to an external field affecting the flux of emitted internal charged particles;
(iii) during the power supply to the sample, measuring the emitted charged particles versus their energy thereby extracting local potential values at chemical entities of the sample; thereby enabling characterization of accumulation of charge within at least one region of the sample.

According to yet another aspect of the invention, there is provided a method for measuring the electrical properties of a sample, the method comprising:
(i) exciting the sample with high energy radiation to cause emission of internal charged particles from the sample;
(ii) supplying electrical power to a circuit formed by the sample and any added component connected to a back contact of the sample, said supplying of electric power comprising irradiating the circuit by low energy charged particles, and applying bias voltage to the back contact of the sample;
(iii) during the power supply to the sample, measuring the emitted charged particles versus their energy thereby extracting local potential values at chemical entities of the sample; thereby enabling characterization of accumulation of charge within at least one region of the sample.

According to yet another aspect of the invention, there is provided a method for measuring the electrical properties of a sample, the method comprising:
(i) exciting the sample with high energy radiation to cause emission of internal charged particles from the sample;
(ii) supplying electrical power to a circuit formed by the sample and any added component connected to a back contact of the sample, said supplying of electric power comprising at least one of the following: irradiating the circuit by low energy charged particles, subjecting the circuit to an external field affecting the flux of emitted internal charged particles, and supplying a bias voltage to the back contact of the sample;
(iii) affecting the sample by external electromagnetic radiation;
(iv) during the power supply to the sample and illumination of the sample, measuring the emitted charged particles versus their energy thereby extracting local potential values at chemical entities of the sample; thereby enabling determination of at least one of photo voltage and photo current of the sample.

According to yet another broad aspect of the present invention, there is provided a device for usage in measuring electrical properties of a sample, the device comprising:
(a) an excitation source configured and operable to generate high energy radiation to be applied to the sample to cause emission of internal charged particles from the sample;
(b) an electric power supply system associated with a circuit formed by the sample and any added component connected to a back contact of the sample, said electric power supply system comprising at least one of the following: a source of charged particles operable to irradiate the sample with a beam of low energy charged particles; a source of an external field affecting the flux of the emitted charged particles; and a voltage supply unit operable to supply bias voltage to the back contact of the sample; and
(c) a detection system including at least one of the following: a voltmeter for accommodating at a distance from the sample and comprising a charged particles' spectrometer for contactless detecting and analyzing the emitted charged particles versus their energy, and thus extracting local potentials of different chemical entities in the sample and generating measured data indicative thereof; and an ampermeter for measuring an electric current through the sample;

the device being thereby operable for providing at least one of the following:

determination of spectrally resolved I–V characteristic of the sample;

evaluation of a work function characteristic of the sample; characterization of electric leakage or breakdown conditions of the sample; and characterization of accumulation of charge within at least one region of the sample.

The device may also include an electronic device including for example external resistance unit(s) and/or capacitance unit(s) and/or a controlled contact to ground.

According to yet another aspect of the invention, there is provided a device for use in measuring electrical properties of a sample, the device comprising:

(a) an excitation source configured and operable to generate high energy radiation to be applied to the sample to cause emission of internal charged particles from the sample;

(b) an electric power supply system associated with a circuit formed by the sample and any added component connected to a back contact of the sample, said electric power supply system comprising at least one of the following: a source of charged particles operable to irradiate the sample with a low energy charged particles' beam, a source of external field for affecting the flux of the emitted charged particles, and a voltage supply unit for supplying bias voltage to the back contact of the sample;

(c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;

the device being therefore operable for determining a spectrally resolved I–V characteristic of the sample.

According to yet another aspect of the invention, there is provided a device for use in measuring electrical properties of a sample, the device comprising:

(a) an excitation source configured and operable to generate high energy radiation to be applied to the sample to cause emission of internal charged particles from the sample;

(b) an electric power supply system associated with a circuit formed by the sample and any added component connected to a back contact of the sample, said electric power supply system comprising at least one of the following: a source of charged particles operable to irradiate the sample with a low energy charged particles' beam, a source of external field for affecting the flux of the emitted charged particles, and a voltage supply unit for supplying bias voltage to the back contact of the sample;

(c) a detection system including: a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof; and at least one ampermeter for measuring an electric current through the sample;

the device being therefore operable for determining a spectrally resolved I–V characteristic of the sample.

According to yet another aspect of the invention, there is provided a device for use in measuring electrical properties of a sample, the device comprising:

(a) an excitation source configured and operable to generate high energy radiation to be applied to the sample to cause emission of internal charged particles from the sample;

(b) an illumination assembly operable to affect the sample by external electromagnetic radiation;

(c) an electric power supply system associated with a circuit formed by the sample and any added component connected to a back contact of the sample, said electric power supply system comprising at least one of the following: a source of charged particles operable to irradiate the sample with a low energy charged particles' beam, a source of external field for affecting the flux of emitted charged particles, and a voltage supply unit for supplying bias voltage to the back contact of the sample;

(d) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;

the device being therefore operable for determining at least one of photo voltage and photo current of the sample.

According to yet another aspect of the invention, there is provided a device for use in measuring electrical properties of a sample, the device comprising:

(a) an excitation source configured and operable to generate high energy radiation to be applied to the sample to cause emission of internal charged particles from the sample;

(b) an illumination assembly operable to affect the sample by external electromagnetic radiation;

(c) an electric power supply system associated with a circuit formed by the sample and any added component connected to a back contact of the sample, said electric power supply system comprising at least one of the following: a source of charged particles operable to irradiate the sample with a low energy charged particles' beam, a source of external field for affecting the flux of emitted charged particles, and a voltage supply unit for supplying bias voltage to the back contact of the sample;

(d) a detection system including: a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof; and at least one ampermeter for measuring an electric current through the sample;

the device being therefore operable for determining at least one of photo voltage and photo current of the sample.

According to yet another aspect of the invention, there is provided a device for use in measuring electrical properties of a sample, the device comprising:
- (a) an excitation source configured and operable to generate high energy radiation to be applied to the sample to cause emission of internal charged particles from the sample;
- (b) an electric power supply system associated with a circuit formed by the sample and any added component connected to a back contact of the sample, said electric power supply system comprising a source of charged particles operable to irradiate the sample with a low energy charged particles' beam, and at least one of the following: a voltage supply unit for supplying bias voltage to the back contact of the sample, and a source of external field for affecting the flux of the emitted charged particles;
- (c) a detection system including: a voltmeter for accommodating at a distance from the circuit and comprising a charged particles' spectrometer for contactless detecting and analyzing the emitted charged particles versus their energy and therefore extracting local potentials of different chemical entities in the sample, and generating measured data indicative thereof;

the device being therefore operable for evaluating a work function of the sample.

According to yet another aspect of the invention, there is provided a device for use in measuring electrical properties of a sample, the device comprising:
- (a) an excitation source configured and operable to generate high energy radiation to be applied to the sample to cause emission of internal charged particles from the sample;
- (b) an electric power supply system associated with a circuit formed by the sample and any added component connected to a back contact of the sample, said electric power supply system comprising a source of charged particles operable to irradiate the sample with a low energy charged particles' beam, and at least one of the following: a voltage supply unit for supplying bias voltage to the back contact of the sample, and a source of external field for affecting the flux of the emitted charged particles;
- (c) a detection system including: a voltmeter for accommodating at a distance from the circuit and comprising a charged particles' spectrometer for contactless detecting and analyzing the emitted charged particles versus their energy and therefore extracting local potentials of different chemical entities in the sample, and generating measured data indicative thereof; and at least one ampermeter for measuring an electric current through the sample;

the device being therefore operable for evaluating a work function of the sample.

According to yet another aspect of the invention, there is provided a device for use in measuring electrical properties of a sample, the device comprising:
- (a) an excitation source configured and operable to generate high energy radiation to be applied to the sample to cause emission of internal charged particles from the sample;
- (b) an electric power supply system associated with a circuit formed by the sample and any added component connected to a back contact of the sample, said electric power supply system comprising a source of charged particles operable to irradiate the sample with a low energy charged particles' beam, and at least one of the following: a voltage supply unit for supplying bias voltage to the back contact of the sample, and a source of external field for affecting the flux of the emitted charged particles; and
- (c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;

the device being therefore operable for providing characterization of electric leakage or breakdown conditions of the sample.

According to yet another aspect of the invention, there is provided a device for use in measuring electrical properties of a sample, the device comprising:
- (a) an excitation source configured and operable to generate high energy radiation to be applied to the sample to cause emission of internal charged particles from the sample;
- (b) an electric power supply system associated with a circuit formed by the sample and any added component connected to a back contact of the sample, said electric power supply system comprising a source of charged particles operable to irradiate the sample with a low energy charged particles' beam, and a voltage supply unit for supplying bias voltage to the back contact of the sample; and
- (c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;

the device being therefore operable for providing characterization of electric leakage or breakdown conditions of the sample.

According to yet another aspect of the invention, there is provided a device for use in measuring electrical properties of a sample, the device comprising:
- (a) an excitation source configured and operable to generate high energy radiation to be applied to the sample to cause emission of internal charged particles from the sample;
- (b) an electric power supply system associated with a circuit formed by the sample and any added component connected to a back contact of the sample, said electric power supply system comprising a source of charged particles operable to irradiate the sample with a low energy charged particles' beam, and at least one of the following: a voltage supply unit for supplying bias voltage to the back contact of the sample, and a source of external field for affecting the flux of the emitted charged particles; and
- (c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;

the device being therefore operable for providing characterization of accumulation of charge within at least one region of the sample.

According to yet another aspect of the invention, there is provided a device for use in measuring electrical properties of a sample, the device comprising:

(a) an excitation source configured and operable to generate high energy radiation to be applied to the sample to cause emission of internal charged particles from the sample;

(b) an electric power supply system associated with a circuit formed by the sample and any added component connected to a back contact of the sample, said electric power supply system comprising a source of charged particles operable to irradiate the sample with a low energy charged particles' beam, and a voltage supply unit for supplying bias voltage to the back contact of the sample; and (c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof, the device being therefore operable for providing characterization of accumulation of charge within at least one region of the sample.

BRIEF DESCRIPTION OF THE DRAWINGS

In order to understand the invention and to see how it may be carried out in practice, preferred embodiments will now be described, by way of non-limiting example only, with reference to the accompanying drawings, in which:

FIGS. 9 and 10 illustrate the experimental results of photovoltage measurements in CdSe films on Si, wherein FIG. 9 shows the photovoltage as a function of electric current through the sample of a p-type CdSe film on Si, for the cases of varying eFG electron energy and fixed electron energy; and FIG. 10 shows the measurement of photocurrent as a function of total current, where the current is changed by the X-ray source power with no eFG input.

DETAILED DESCRIPTION OF THE INVENTION

Figure 1:
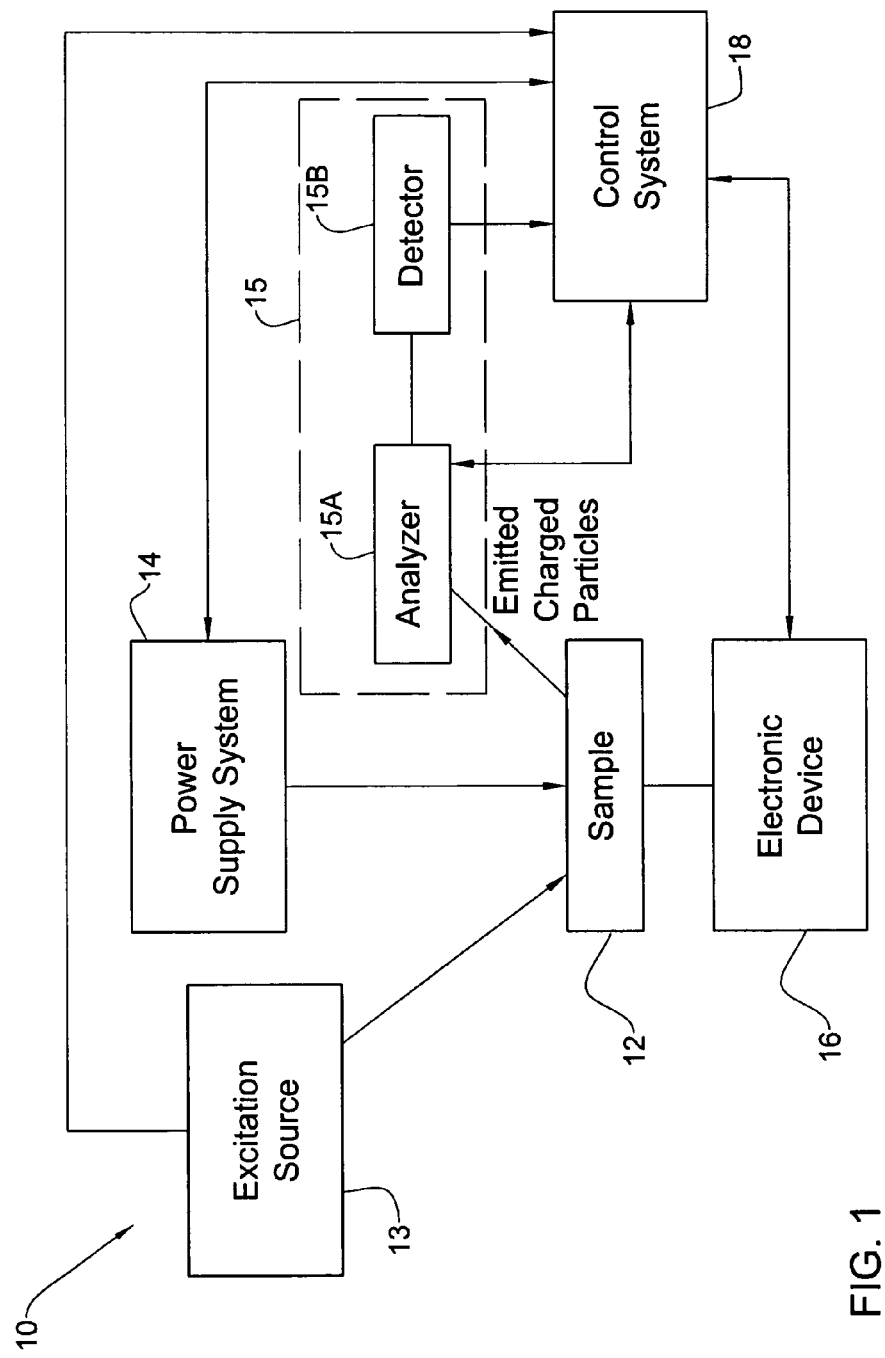
FIG. 1 is a block diagram of the main components of a device of the present invention for electrical measurements in a sample.

Referring to FIG. 1, there is illustrated, by way of a block diagram, a device 10 according to the invention for chemically resolved electrical measurements in a sample 12. The sample 12 may and may not be composed of several components of different materials, and may include small structures ranging from the nanoscale up to micrometer and larger scales.

The device 10 comprises such main constructional parts as an excitation source 13 of the kind capable of generating high energy radiation to cause emission of internal charged particles from the sample; a power supply system 14; a detection system 15 including an analyzer 15A and a detector 15B connected to the output of the analyzer 15A; and optionally includes an electronic device 16 associated with the back contact of the sample 12. A control system 18 is provided being connectable to the elements of the device 10.

The excitation source 13 may include a source of monochromatic electromagnetic radiation such as X-ray beam, and/or an e-beam source, and/or an ion beam source.

The power supply system 14 may include a source of low energy charged particles (preferably, yet not limited to, up to 10 eV in kinetic energy). Alternatively or additionally, the power supply to the sample may be achieved by a source of external field. Additionally, the power supply system may include a voltage supply unit for supplying bias voltage to the back contact of the sample. The charged particles' source 14 may include a source of low energy electrons or a source of slow ions (e.g., $He^+$-beam).

The detection system, namely its analyzer 15A, may include a charged particles' spectrometer for measuring local potential values at different chemical entities of the sample. Alternatively or additionally, the detection system may include at least one amperometer for measuring an electric current through the sample.

The electronic device 16 may for example include a variable external resistor.

The control system 18 is typically a computerized system, including inter alia a memory utility, a data processing and analyzing utility, a setting utility (for operating the charged particles' source 14, the electronic device 16, and when necessary—any additional unit); and a suitable interface utility.

Figure 2A:
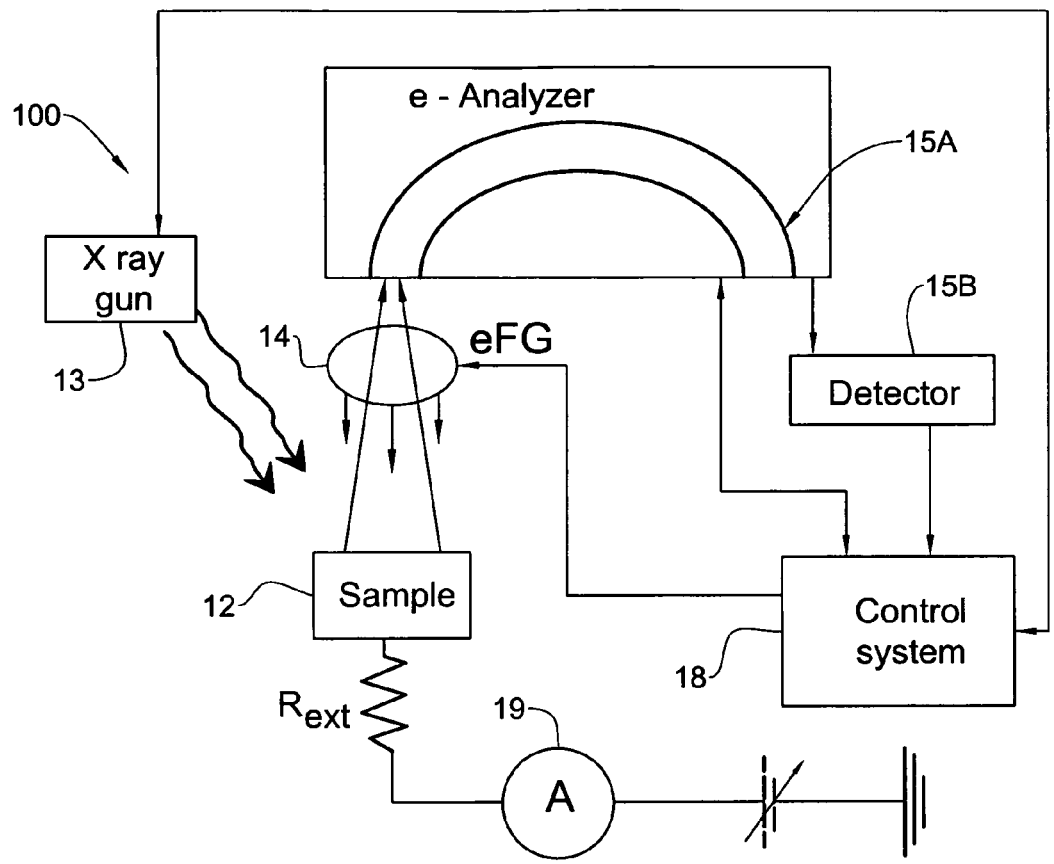
FIG. 2A illustrates one specific example of the generalized electric circuitry of the device of the present invention utilizing the XPS-based electric measurements.
Figure 2B:
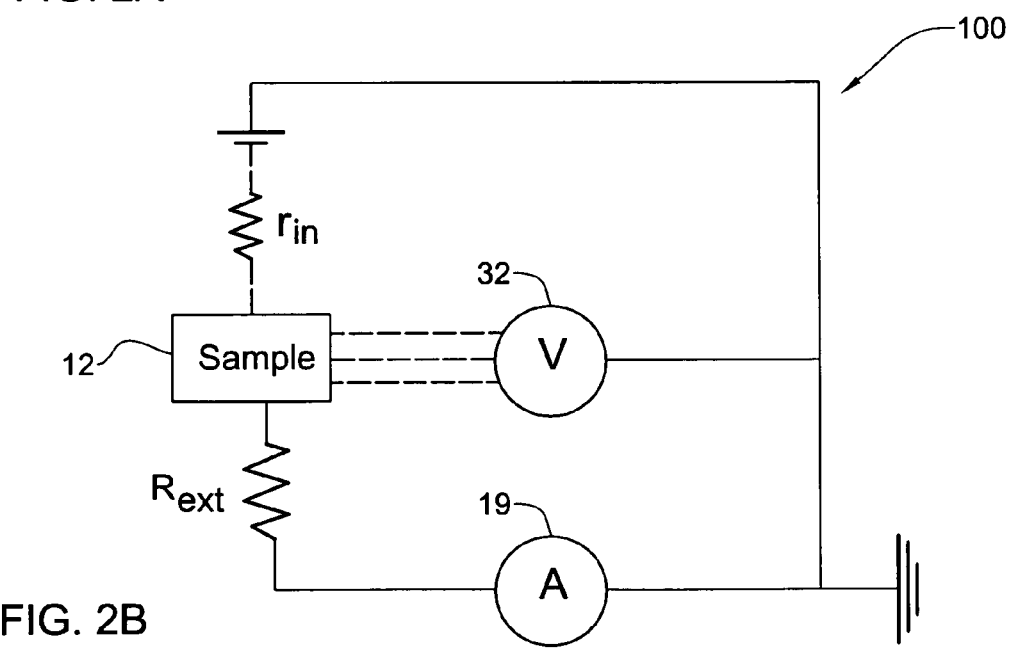
FIG. 2B illustrates the analog circuit of the device of FIG. 2A.

The device of the present invention can be configured for measuring the I–V characteristic of a sample. An example of the device configuration for this application is more specifically illustrated in FIGS. 2A and 2B showing, respectively, the main constructional components of a measuring device 100 applied to a sample 12, and a simplified analogue circuit of the device 100, where dashed lines stand for non-wired currents. The same reference numbers are used for identifying those components, which are common in all the embodiments of the invention.

For the purpose of I–V measurements, the detection system (15 in FIG. 1) includes an ampermeter 19 operable to measure an electric current through the sample 12. In this specific example of FIGS. 2A–2B, an XPS unit is used. It should however be understood that XPS may be replaced by any other suitable tool. The XPS unit may be of any known type. Its construction and operation are known per se and therefore need not be specifically described except for noting that the XPS unit is equipped with suitable electron optics and includes the X-ray beam source 13, the source of low-energy electrons (electron flood gun) 14 and the analyzer 15A.

An X-ray beam produced by the source 13 impinges on the surface region of the sample 12, resulting in the emission of photoelectrons. Photoelectrons emerging from a selected portion of the sample region are directed into the analyzer 15A and the output of the analyzer is received at the detector 15B that generates data indicative of the detected photoelectrons. This data is received at the control unit 18, where it is processed by the data processing and analyzing utility to obtain the resulting spectral analysis information and store it in the memory utility. The operation of the electron flood gun 14 is controlled by the setting utility of the control unit 18 to provide the appropriate flood gun flux and bias voltage values in a desired manner. The electric current through the sample is measured by the ampermeter 19.

Thus, the electrical circuit of the device 100 includes two beams of electrons—a beam of low energy electrons produced at the electron flood gun (eFG) 14 and projected onto the sample surface, and a beam of internal electrons that are ejected from the sample by the X-ray source 13 and directed via an electron lens system (not shown) to be received by the analyzer 15A and be detected at its exit by the detector 15B. Considering the conventional configuration of the XPS unit, the beam of slow electrons is controlled via at least two bias voltages ($V_G$ and $V_F$) and filament current ($I_F$).

It should be understood that in all the figures, an eFG constitutes a source of low-energy charged particles, e.g., electrons' or ions' source.

Thus, the power supply in this circuit is a distant source of slow electrons (eFG) [8]. Though not physically attached to the specimen, it presents an optimal electrical contact, free of contact defects and inter-atomic (condensed matter) interactions. With some reservations, the eFG beam may be treated as a metallic electrode of null work function. This power supply advantageously allows application of additional distant tools directly onto the studied surface. A distant multi-channel voltmeter 32 (FIG. 2B) corresponds to the X-ray gun, the spectrometer (analyzer and detector units 15A and 15B in FIG. 2A) and to components directing the emitted internal electrons into the analyzer (i.e., an electronic lens system, which is not specifically shown). This voltmeter reads local potential values from line positions [1]. Different lines recorded by this spectrometer represent different chemical entities. Thus, with predetermined chemical characteristics, an inherent aspect of system design, each spectral line can serve as a channel for local potential measurements. This voltmeter can probe quite deep regions, down to about 15 nm. The requirement for small currents flowing through a voltmeter is reasonably matched: Typical photocurrents here are 0.1–1 nA, while the eFG currents are three orders of magnitude larger. Moreover, the assumptions on the 'already known' structure can be checked here, in-situ, by a powerful analytical technique, XPS.

When the effective resistance ($R_{eff}$) of the circuit (formed by the sample 12 and its back contact component(s)) is sufficiently high, the (finite) eFG source becomes voltage limited, and hence functions as a battery, namely, the resultant potential at the sample surface ($V_s$) follows the eFG bias voltages, with slight deviations, which are describable by an internal resistance parameter $r_{in}$. In this case, charge accumulation raises the surface potential, thus slowing the eFG electrons until a steady-state is reached, where the incoming flux of electrons balances with the total flux leaving the surface, both to the vacuum and to the back contact. On the other hand, at the limit of low resistance, the eFG source is current limited, serving as a current supply. It should be noted that the voltage-limited situation can be always matched by adding back resistors. Having direct feedback on the actual surface potential, a full control of the effective eFG impact is established.

The following are the results of experiments carried out with the technique of the present invention.

Figure 3A:
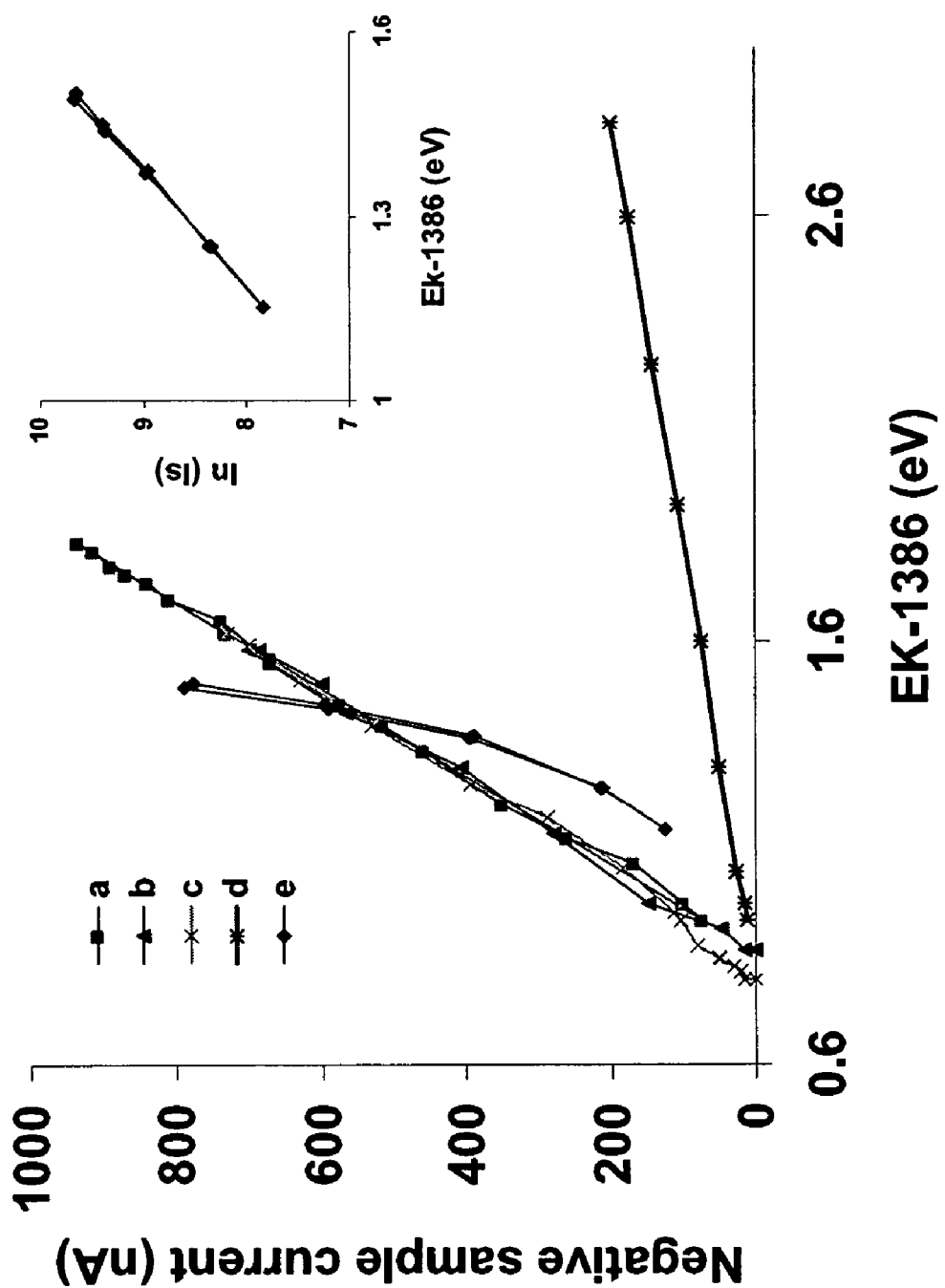
FIGS. 3A–3B and 4A–4B illustrate experimental results of electric measurements of the I–V characteristic of several samples obtained with the device of FIGS. 2A–2B.

FIG. 3A illustrates the results of the XPS-based electric measurements performed with the above-described device 100. In these experiments, two samples were measured—n-doped and p-doped Si. Si wafers, n- and p-type, were HF-etched and washed in deionized water, then exposed to various conditions. Conductive double-sided carbon tape, and in several cases InGa, were used at the sample-holder contact. The measurements were performed on a slightly modified Kratos AXIS-HS setup (XPS instrument), using monochromatic Al(kα) radiation at source power of 15–150 W. The electron flood-gun (eFG) conditions were controlled via filament current ($I_F$) and two bias voltages ($V_G$ and $V_F$), its beam diameter, on a scale of a few millimeters, subjected to variations upon changes in bias values. An external Keithley 487 electrometer and additional known resistors were connected to the back contact of the sample. The electrometer was operated to record the total current flowing through the sample. Spectral line shifts were derived at accuracy of 10–50 meV, depending on noise level and spectral stability.

The measurement results shown in FIG. 3A present I–V curves obtained by plotting the (negative) sample-current ($I_S$) vs kinetic energy (Ek) of the Si (2 $p_{3/2}$) (non-oxidized) line. Curves a–d correspond to highly doped n-Si. The slope of the various curves is just the effective impedance between the sample surface and ground, practically independent of the choice of eFG parameters. Curve e presents a different case recorded with p-Si. Exponential I–V dependence is observed here (see inset), arising from the back contact, where the double-sided tape creates a Schottky-type junction with the wafer. Back impedance is 1 MΩ in all the curves, except for curve d, where $R_{ext}$=10 MΩ. The varied eFG parameters are as follows: (a) filament current; (b) bias voltages; (c) bias voltages in a different combination; and (d) same as (c), but with different back resistance.

As shown, both samples indicate regular circuitry performance, which obeys common rules and hence applicable to various systems. The regular behavior of these measurements indicates that the circuit does not consist of non-passive components.

These experiments illustrate the elimination of top-contact problems in direct electrical measurements. As further shown in FIG. 3B, the technique of the present invention (CREM—chemically resolved electrical measurements) provides for chemically discriminating the I–V information. Here, element specific I–V plots are illustrated, showing the electrical behavior at selected regions within a three component heterostructure across the surface of a Si wafer: the wafer itself—given by the main Si line, its surface oxide (the oxide layer, evaluated in-situ by angle resolved XPS, is homogeneous, 2.0 nm thick)—given by the Si(ox) and O lines, a carbonic overlayer—given by the C line. The carbonic layer is prepared by intensively (20 hours) irradiating a self-assembled monolayer with X-rays, thus releasing most of its hydrogen. The total loss of carbon in this process is about 3% only. In-situ thickness evaluation yields here ca. 2.2 nm. In this figure, an arbitrary zero is chosen for the kinetic energy scale. Bias eFG is varied here in the range of 3.3–4.5 V The so-obtained curves can be easily translated into zone-specific data. For example, the resistance of the buried oxide layer is derived from a difference curve, Si(ox)-Si, yielding 0.83 MΩ/nm. Similarly, the carbonic layer resistance is found to be 0.53 MΩ/nm.

It should be noted that the accuracy of local potential determination is subjected to the actual potential gradients across the probed volume. Practically, however, this broadening effect is largely suppressed by the attenuation effects and further by analyzing relative shifts only, more specifically the shifts of the right hand-side (high kinetic energy) line-edge [1]. In the present case, the derived values can be assigned to the top of each corresponding layer. The accuracy of this assignment has been estimated with top markers to be better than 0.4 nm. Further improvement is possible by convoluting the bare line-shape with a function describing the potential drop and the corresponding signal attenuation.

The role of contacts in measuring molecular layers is critical, even when metallic surfaces can be applied. Evidently, with semiconducting or dielectric surfaces to which the molecules are attached, this point becomes crucial for understanding the properties of the layer itself. Thus, the invented technique of the present invention provides for easily subtracting all substrate contributions and extracting the properties of the region of interest.

Considering measurement of the conductance through a molecular layer (an intriguing subject, which exhibits major technical difficulties), even with non-metallic substrates, all contact contributions are removable, as shown above. However, since molecular systems frequently present poor electrical stability, the CREM measurements might be too slow and the X-irradiation might tend to induce sample damage, to which electric measurements are usually highly sensitive.

Figure 4A:
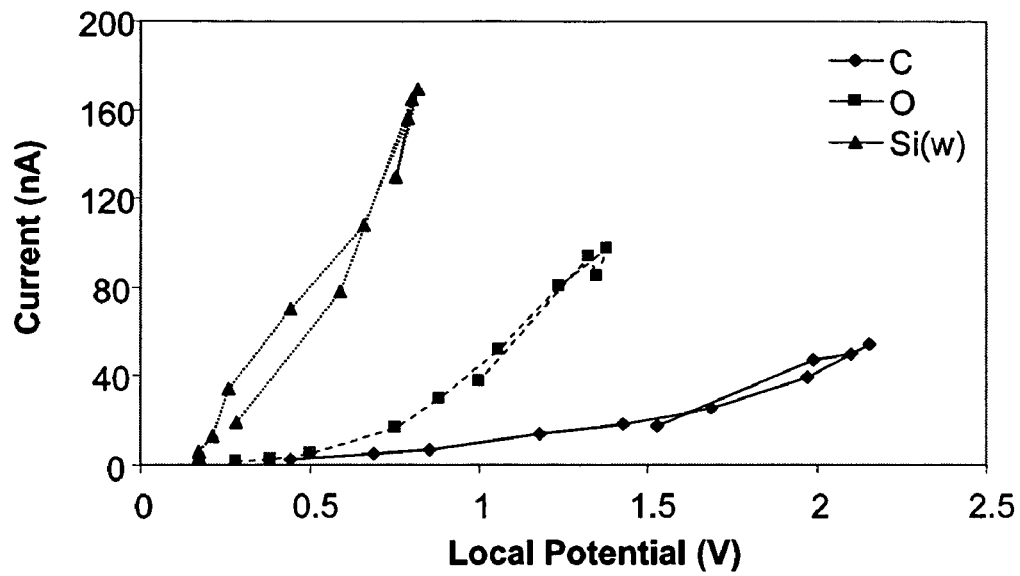
Figure 4B:
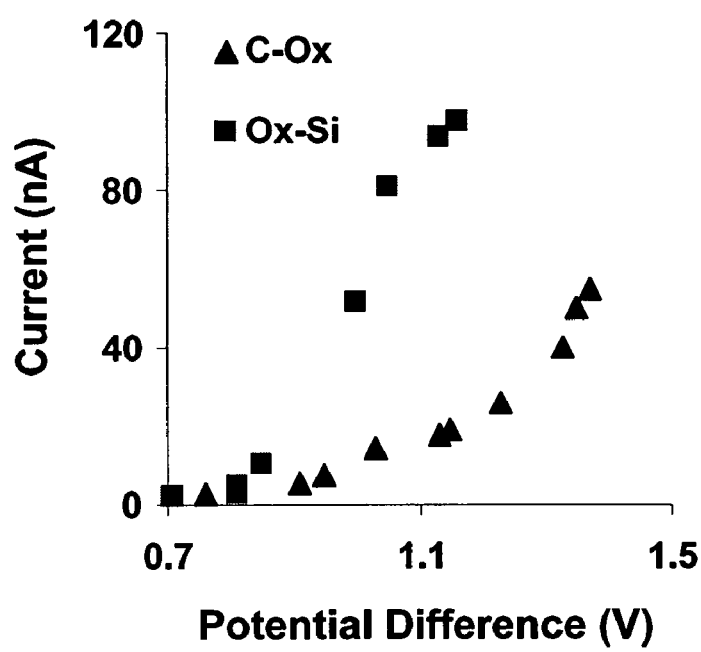

The present invention provides for overcoming the above problem. This is illustrated in FIGS. 4A and 4B presenting the results of measuring self-assembled layer conductance—a high-quality self-assembled monolayer (SAM), $NH_2C_{20}Si$, on p-Si. Here, the application of varying eFG voltages in the 2–5 V range to $NH_2C_{20}Si$ self-assembled monolayer on p-Si was used. A relatively large sample was used here, ca 2×4 cm, its lateral uniformity well confirmed, such that several fresh areas could be tested for each element-specific curve.

In FIG. 4A, element specific plots represent selected regions: the organic layer (C), the Si-oxide (O) and the wafer (Si). In FIG. 4B, difference curves are shown—C—Ox and Ox—Si exhibiting the net response of the organic monolayer and the (inner) oxide, respectively. The slight hysteresis in FIG. 4A arises from scanning a bit faster than the response time of the system (irreversible sample degradation is observable at longer time scales). Current evolution with time due to increasing density of defects has been evaluated and accounted for in FIG. 4B.

Figure 3B:
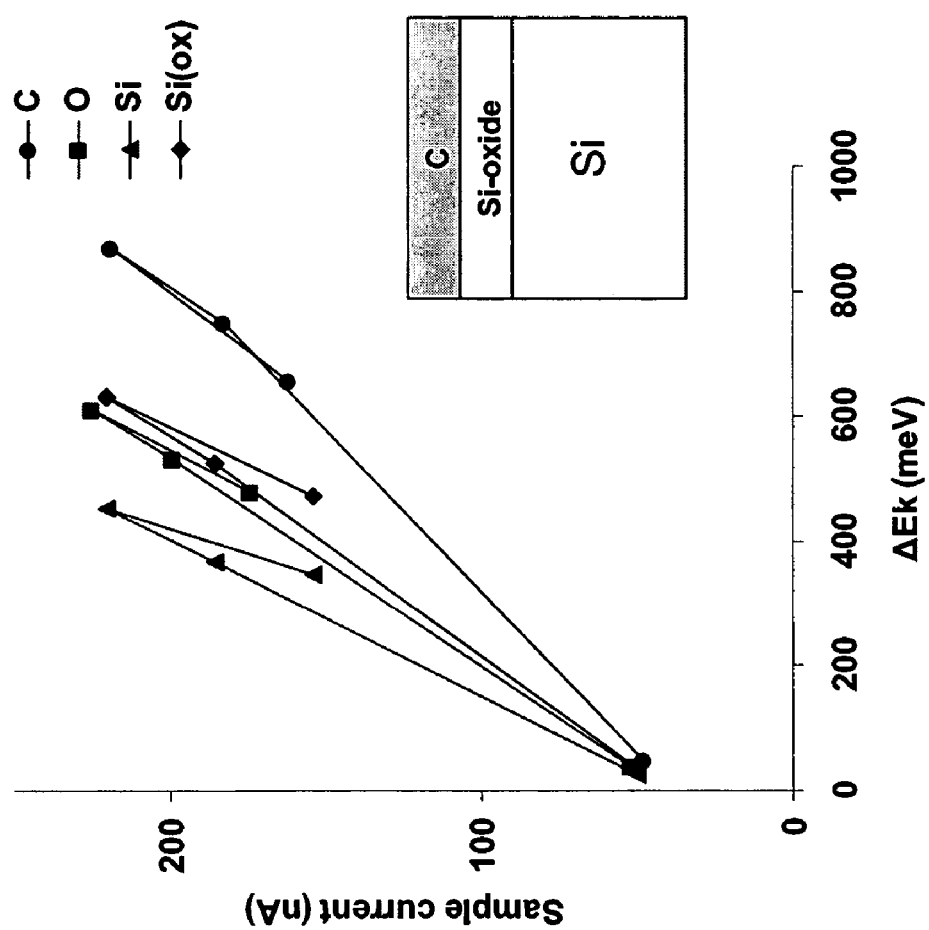

The elements in FIG. 4A represent regions similar to those in FIG. 3B.

Energies are referred to the non-charged state (minimal X-ray power and eFG-off conditions), thus presenting an absolute potential scale. The 'non-damaged' limit has been achieved by cooling to ca 200 K and recording rapidly the line shifts (at a compromised accuracy). Nitrogen detection required slower scans, therefore not included in the figure.

FIG. 4B shows difference I–V curves, 'C—Ox' for the 'contact free' hydrocarbon layer and 'Ox—Si' representing the buried oxide layer net response. The former curve is roughly exponential, suggesting that tunneling mechanisms take place here. It is stressed that the given voltage values are those actually developed at the film surface. The current, on the other hand, includes also ballistic electrons, crossing the layer without reaching thermodynamic equilibrium. In the present measurement, remaining in the 'voltage limited' situation, the ballistic current is constrained to be roughly constant, on the order of a few nA only. Thus, the curve in FIG. 4B represents reliably the current associated with charges accumulated at the surface.

Figure 4C:
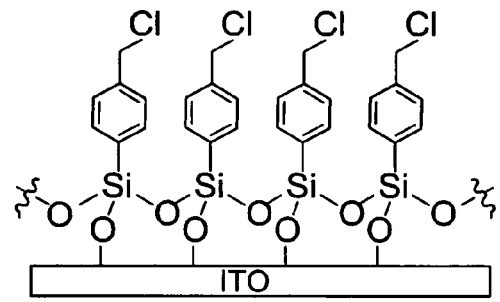
FIGS. 4C to 4E show yet another experimental results of using the CREM of the present invention in X-ray photoelectron spectroscopy to directly probe sub-molecular electrical properties of organic monolayers on ITO.
Figure 4D:
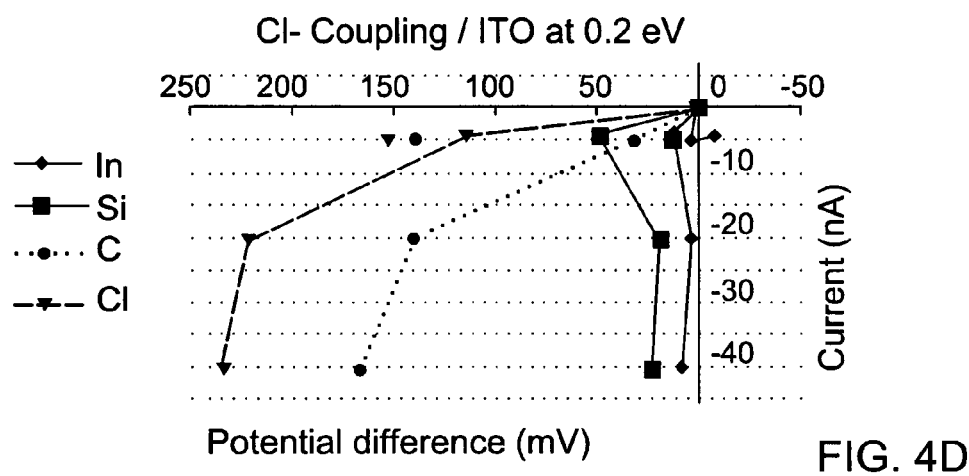
Figure 4E:
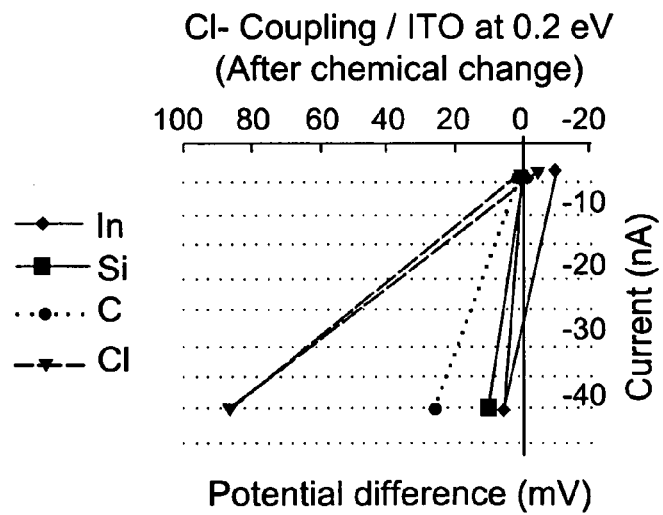

FIGS. 4C to 4E show yet another experimental results obtained with the technique of the present invention, consisting of using CREM in X-ray photoelectron spectroscopy to directly probe the electrical properties of organic layers on ITO at the sub-molecular scale. In the present example, the I–V characteristic of a sample constructed from line-shifts data of specific molecular sites within Cl-benzo-silanes on ITO is measured. FIG. 4C shows the system under measurements, i.e., molecules on a substrate of ITO. FIG. 4D shows the experimental results in the form of chemically resolved I–V curves of the system of FIG. 4C under the fixed eFG beam energy. FIG. 4E shows the I–V curves corresponding to the same experimental conditions but analyzed after the system, which has undergone structural changes at early stages of the experiment, is stabilized. The invented technique presents a novel level of electrical reading capabilities at selected atomic sites, with superior sensitivity to fine electrochemical modifications.

The present invention also provides for evaluation of the material work function, based on recording the shift of X-ray photoelectron signals from a surface irradiated by low energy electrons. This technique provides for measuring samples with very low conductivity, poor back contacts, and high dielectric constant. The method is also applicable to magnetic materials and can be particularly effective for studies of multilayer and heterogeneous systems. The evaluation of the material work function is achieved by application of bias voltage(s) to the back contact of the sample and/or to the low energy beam of charged particles (i.e., by applying an external field affecting the internal charged particles flux from the sample, e.g., by using a grid electrode). For example, the eFG parameters and/or bias voltage may vary during the measurements.

It should be noted that the methods of the present invention are not limited to XPS-based set-ups. Additional spectroscopies of charged particles, where chemical and electrical information can be correlated, e.g. Auger electron spectroscopy (AES), can similarly become successful templates for CREM. The technique of the present invention may successfully replace existing electrical tools in various applications.

Figure 5:
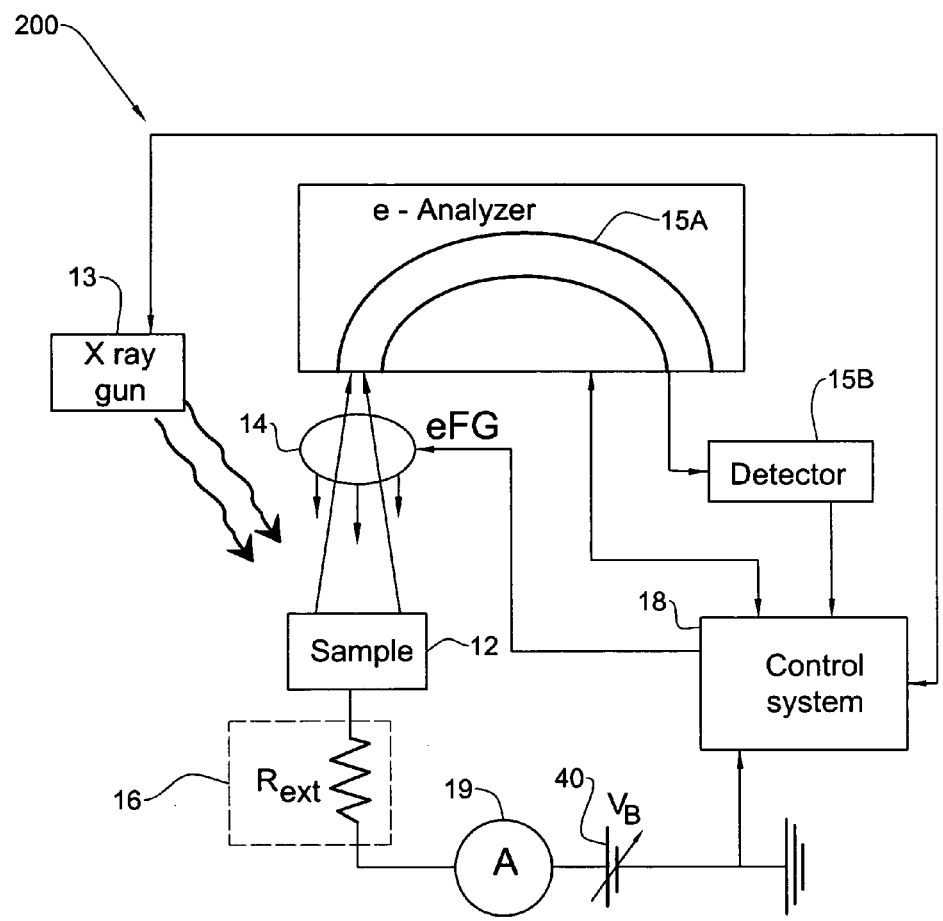
FIG. 5 illustrates a measurement device according to another embodiment of the present invention.

Reference is now made to FIG. 5 exemplifying a device 200 according to another embodiment of the invention for measuring in a sample 12. The device 200 comprises an excitation source 13 (X-ray beam source in the present example) for emitting charged particles (electrons) from the sample; a power supply system including a charged particles' source 14 (electron flood gun), and preferably also includes a voltage supply unit 40 for supplying bias voltage to the back contact of the sample; a detection system including an analyzer 15A (electron spectrometer) and a detector 15B at the output of the spectrometer, and preferably also including an ampermeter 19. An electronic device 16 includes an external resistor $R_{ext}$. A control unit 18 is appropriately provided for operating the device 200 and processing measured data coming from the device. The control unit 18 operates the voltage supply 40 for applying a negative bias to the sample 12.

Figure 6A:
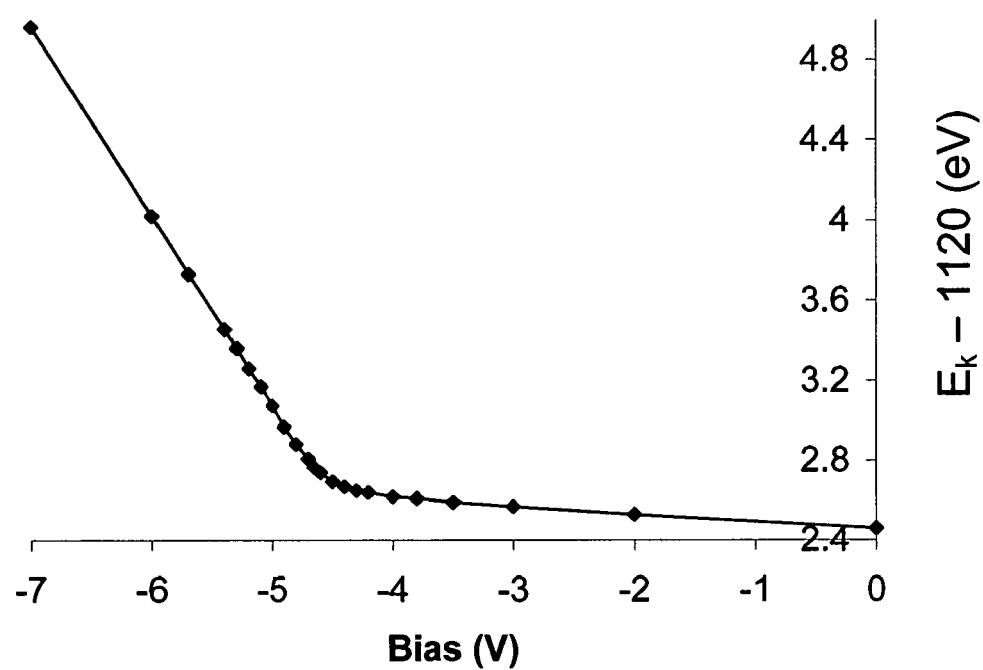
FIG. 6A illustrates the experimental results of using the technique of the present invention (device of FIG. 5) to evaluate the work function of a sample.

FIG. 6A illustrates the experimental results obtained with the above-described device 200 of FIG. 5 for evaluating the work function of a sample including Ag layer on Si. The eFG 14 is operated at (high flux) fixed conditions, while the external resistor $R_{ext}$ at the back contact of the sample 12 assists in approaching the 'voltage limited' conditions for the eFG operation. Ideally, under these conditions the electric field between the sample surface and the eFG approaches zero, namely, the vacuum level near the sample surface is raised by the charging to be very close to the vacuum level at the eFG region (as set via its bias, $V_G$). In addition, the control unit 18 operates the voltage supply unit 40 to apply a variable negative bias ($V_B$) to the back contact of the sample 12. The kinetic energy of a representative element (here, Ag) is then examined as a function of $V_B$.

Various experiments carried out by the inventors have shown that the overall shape of the curve is retained over a broad range of eFG parameters. This overall shape consists of two linear branches, where the crossover region, around an inflection point (or turning point) of the curve, is relatively narrow. The slope of the high-energy branch, where the eFG is totally ineffective, is 1, as expected by theoretical consideration described further below. The turning point (TP) of the curve (at ca.−4.55 V in the present example) appears when the electric field across the sample, as well as between the eFG source and the measured surface, vanishes. At that point, the surface potential (and hence the corresponding eFG beam energy) is equal to the potential at the back contact of the sample.

The inventors have made various characterization experiments that manifest negligible variations in the curve shape due to lateral sample conductance. The test samples show no influence on TP upon changes in the X-ray flux up to a factor of 15.

As indicated above, the turning point of the curve (FIG. 6A) appears when the electric field across the sample vanishes. At that point, the surface potential (and hence the corresponding eFG beam energy) is equal to the potential at the back contact of the sample. Thus, the work function (WF) of the sample can be extracted from the following relation:

$$WF = V_G - |V_B| + WF_0 \quad (1)$$

wherein $V_G$ is the effective voltage at the eFG 14 and $WF_0$ is an effective instrumental work function, representing the eFG (i.e., is a constant of the instrument).

In the example of FIG. 6A, $V_G$=4.6 V, yielding:

$$WF(Ag) = WF_0 - (-0.05)eV = WF_0 + 0.05 \; eV$$

In the general case of a non-capacitive system (it should be noted that these measurements are DC in nature), we have:

$$V_S = V_B + IR;$$

wherein $V_S$ is the surface potential of the sample; R is the total resistance given by the back resistor and the sample itself; $I = I_e + I_x$ is the total current flowing through the sample: $I_e$ and $I_x$ being, respectively, the eFG contribution and the photoemission contribution to the current. The finite power of the eFG can be accounted for by a phenomenological parameter, r, associated with the eFG internal resistance. Thus:

$$I_e = (V_G - V_S)/(r + R)$$

and hence:

$$V_S = V_B/(1+R/r) + V_G/(1+r/R) + \Delta; \; V_S \leq V_G$$

$$V_S = \text{const.} + V_B + \Delta; \; V_S > V_G \quad (2)$$

wherein $\Delta = I_x R$ is a relatively small term arising from the photocurrent, namely electrons ejected by the X-irradiation to the vacuum. The low-energy spectral region of this emission process is sensitive to small external fields and hence undergoes variations upon changes in $V_B$ and $V_G$. Thus, it can slightly affect the turning point, TP, in Eqn 1 above. Eqn. 2 above can be used to evaluate the source internal resistance, r, and hence quantitatively characterize the eFG operation. The experiments carried out by the inventors have shown that the low branch and the TP shift with $V_G$, which is fully consistent with Eqn. 2.

Figure 6B:
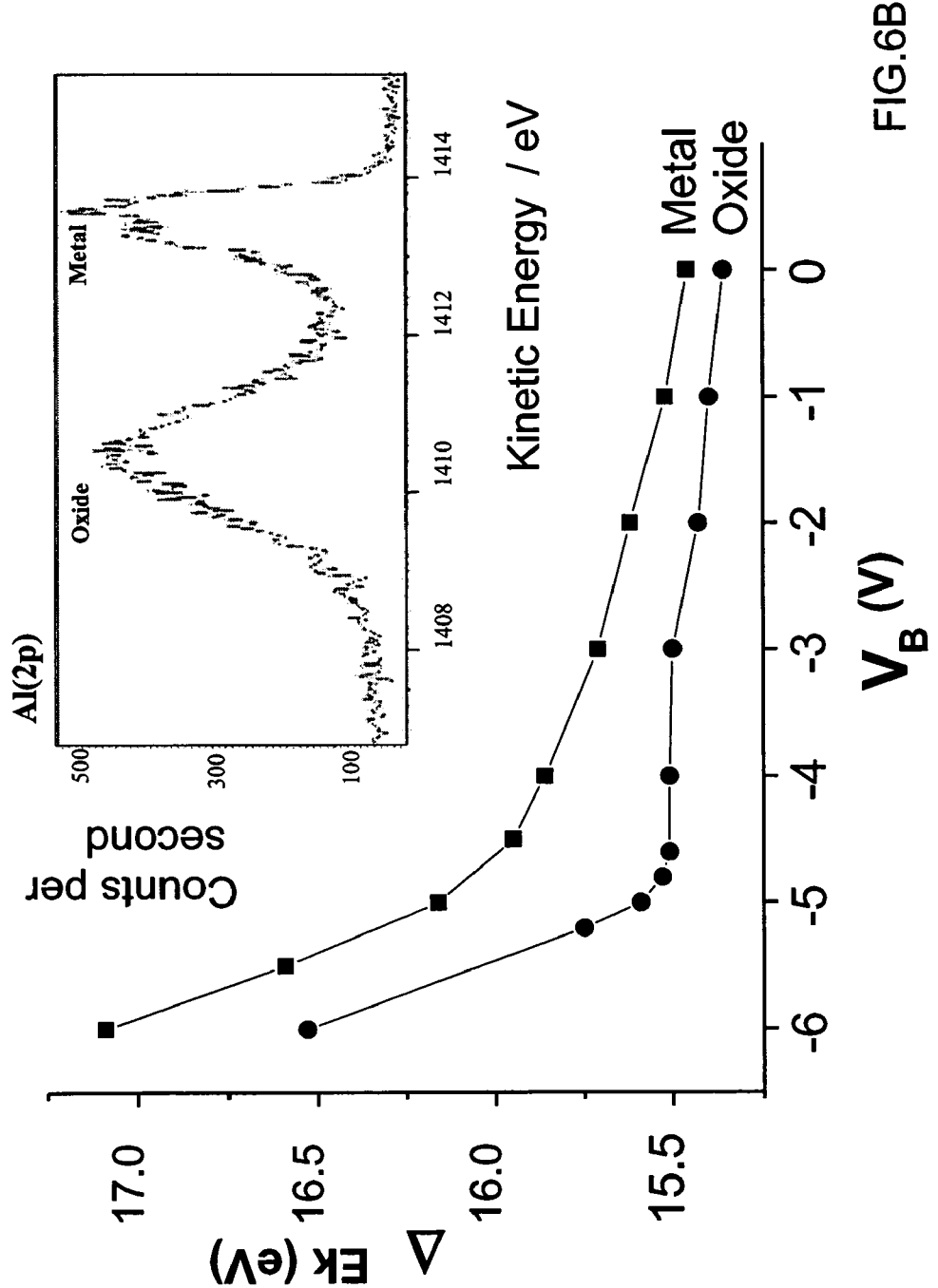
FIG. 6B illustrates further experimental results for separately performed work function measurements for a metal and its oxide, showing chemically resolved electrical XPS (E-XPS) measured curves, and, in the insert of the figure, showing the corresponding spectrum.

The XPS signals of different chemical entities can selectively follow specific regions in a sample. In this connection, reference is made to FIG. 6B, illustrating further experimental results for separately performed measurements for a metal and its oxide. FIG. 6B shows chemically resolved E-XPS curves presenting the difference between an aluminum metallic substrate and its surface oxide. Insert in FIG. 6B shows the corresponding spectrum, with well-resolved metallic and oxidized Al signals. The metallic curve is drawn as Ek-1400 eV, and the oxide curve is vertically shifted to Ek-1402.4 eV The metallic Al substrate and its native oxide exhibit here a significant difference, mainly at the low branch of the curve. The slopes, which depend on the resistance, R, differ due to the surface resistance introduced by the oxide. A relatively broad crossover region characterizes these curves, with somewhat unusual shape for the oxide as being scan-speed dependent. With the chemically resolved curves the surface fields, which tend to distort the work function measurement can be directly analyzed.

The technique of the present invention for the work function evaluation is thus based on referencing the sample to a low-energy electron beam, while performing direct, non-contact readout of the surface potential. This technique uses a flexible electrical reference; as a DC measurement it is relatively insensitive to magnetic and capacitance artifacts, particularly insensitive to the quality of the back contacts. Combined with the in-situ analytical capabilities of XPS, this technique provides a powerful tool for the study of heterogeneous surfaces. The invented method can differentiate between various surface regions, i.e. the metal vs its oxide, as evident from the chemical resolution of this tool. The invented method is technically easy and reliable. Direct mapping of the WF at a lateral resolution of a few micrometers (that is the typical resolution of the new generation of XPS equipment already existing presently) is also possible with this invented method. This presents a considerable improvement over the existing macroscopic probes for WF evaluation.

The CREM of the present invention advantageously provides for studying transport mechanisms through thin dielectric spacers, as well as traps and space-charge distribution within semiconducting systems.

Figure 6C:
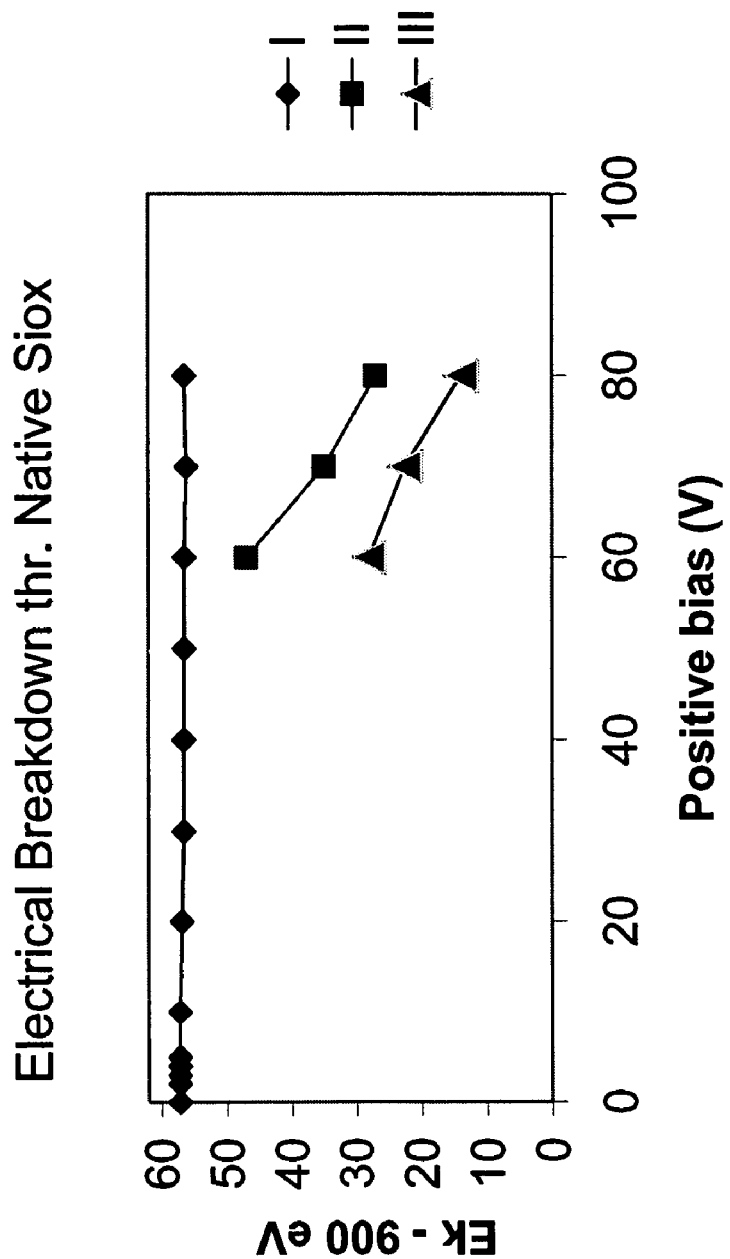
FIGS. 6C and 6D illustrate the experimental results of using the technique of the present invention (device of FIG. 5) to characterize electric breakdown processes across dielectric regions.
Figure 6D:
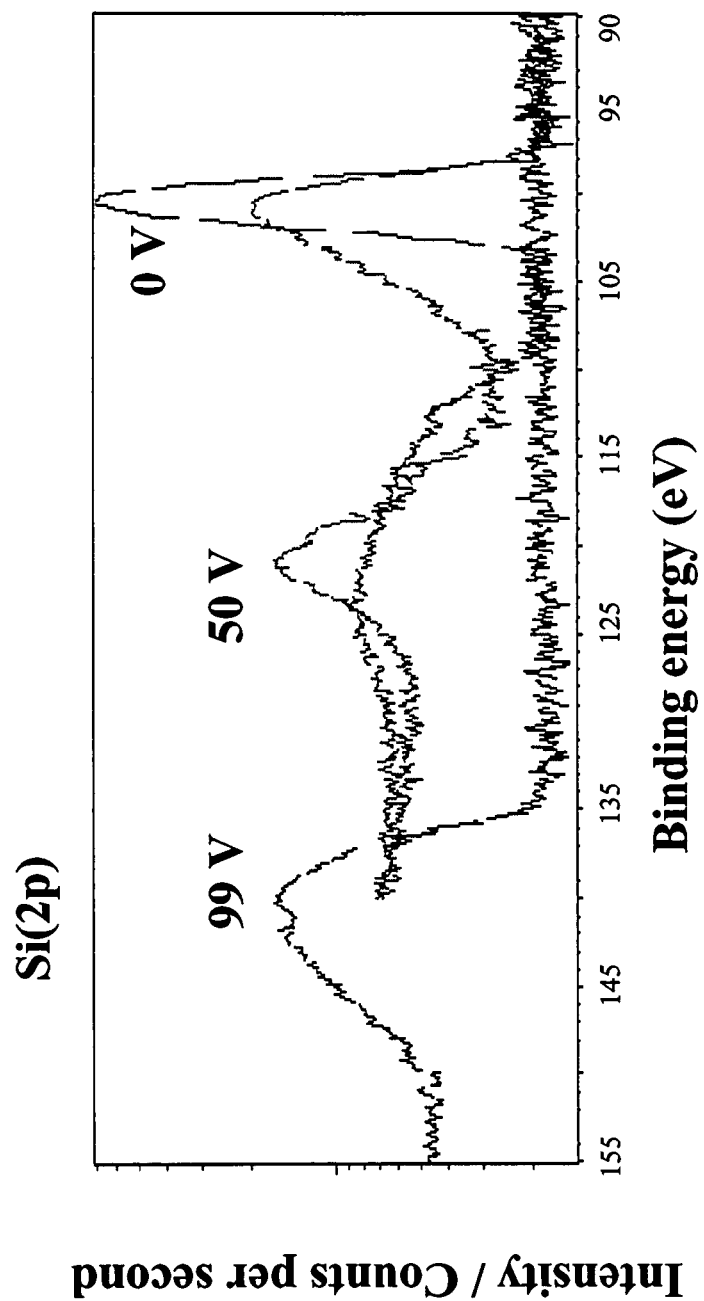

Reference is now made to FIGS. 6C and 6D showing the experimental results of using the technique of the present invention for characterizing electric breakdown or shortcuts across spacers. These experiments are performed with the same instrumentation as used in the work-function measurements, namely the above-described device 200. For the characterization of electric breakdown or shortcuts across spacers, it is useful to detect both the current and the photoelectron energies, while the bias $V_B$ is scanned.

FIG. 6C illustrates the experimental results performed on a sample composed of a fresh native oxide layer on a Si wafer, roughly 80 nm thick, being tested under voltages of 0–100V. A representative XPS line is detected—the O(1s) line. The line positions (given on a kinetic energy scale) of the O(1s) XPS signals are recorded under simultaneous application of top negative charging (with the eFG) and regular (variable) positive bias. Around bias voltage of 70V the intensity of the original line decreases rapidly, while new lines emerge. This figure demonstrates basic observations only, without accounting for the chemical characterization of the defects. The overall potential drop across the oxide is given by the difference between the surface potential, fixed by the eFG, and the back bias potential. At low bias voltages (here, up to 60V), the surface potential remains fixed and the O(1s) line does not show any change (curve I in FIG. 6A). As breakdown processes start to take place, the original line shrinks in intensity (not shown in the figure) but remains at its fixed potential. Correspondingly, new lines (II and III) emerge at lower kinetic energies, gaining intensity as the bias increases. Interestingly, these lines exhibit shifts, which can be used to characterize the electrical properties of the discharge channels. Finally, above the intermediate region (above 80V), the original line fully disappears, indicating that the discharge is efficient enough to affect the entire surface. Curves II and III thus represent regions affected by discharge channels. The latters' intensity increases with the bias voltage (above 60V), while curve I decreases in intensity. It should be noted that curve I remains practically fixed in energy, while curves II and III shift in energy, indicating a finite resistivity along the discharge channels.

FIG. 6D illustrates the breakdown through a different layer of silica, showing three representative spectra of the Si(2p) line. For convenience, the data is presented on a logarithmic intensity scale. The Si signal shows a split in intermediate bias voltages (50V), representing different regions in the sample. At sufficiently elevated bias values, all the detected area leaks. It should be noted that the broad feature of the 0V spectrum (around 110–120 eV) is just a "normal" plasmon band. It should be noted that the invented method allows simultaneous detection of an electric current on the back contact of the specimen. This provides a complementary means for the analysis of the discharge process, as well as for quantifying the leakage currents at early stages (below breakdown).

The technique of the present invention can thus also provide chemical identification of specific electrical regions. This capability is obtained by analyzing different XPS lines. In a complex system this is a critical point. Hence, the present method can directly indicate the "weak point" in a given structure composed of several dielectric spacers, even if this weak link is buried in a sub-surface region. Additionally, considering the failure nature and the discharge mechanisms at the defected channels, the dependence of line position on the bias voltage provides a simple measurement of the effective resistance/capacitance at the relevant domains, independent of their spatial distribution.

Figure 6E:
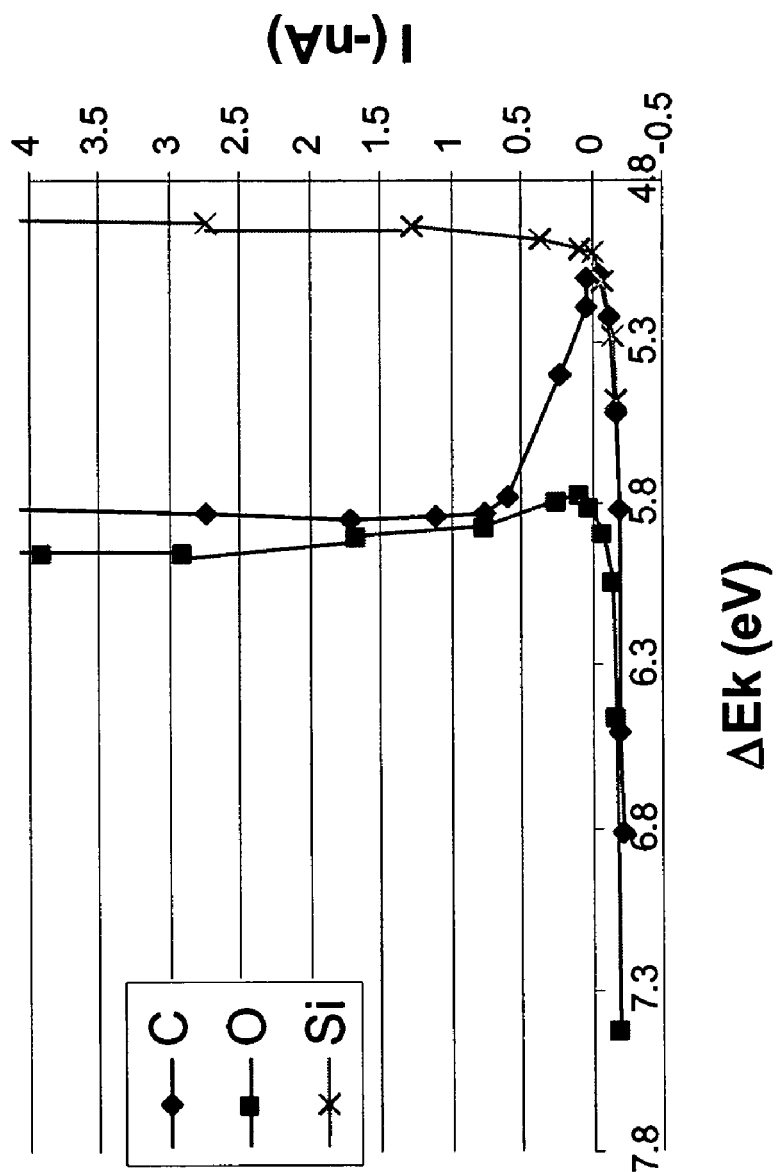
FIG. 6E demonstrates the analysis of charge accumulation at a thin dielectric layer.

FIG. 6E shows the results of an experiment that examines the accumulation of charge within given surface regions. The eFG is set at some given (fixed) conditions, while the sample bias is set at a relatively high negative value, such that no eFG electrons can approach the surface. Then the sample bias is lowered slowly. At the point where eFG electrons start to reach the surface, capacitive regions of the sample can capture electrons, and the electrical potential at those regions rises up. From the change in the potential, one can learn about the amount of trapped charge. The chemical resolution of this analysis provides the identity of the capacitive regions. In the present example of FIG. 6F, a self assembled monolayer (SAM) on a silicon wafer was measured. The Si curve shows a "normal" behavior: as the sample bias ($V_B$) is decreased, the kinetic energy of photoelectrons follows these changes and thus decreases. The (negative) current on the sample (vertical axis in the figure) increases during this scan of $V_B$, due to the increasing flux of incoming eFG electrons. This typical behavior is indeed observed at the Si wafer. In contrast, the organic overlayer starts to trap charges as soon as the eFG electrons can reach the surface. As a result, an increase in the local potential occurs and the C curve turns left, in an opposite tendency to that of the substrate. It should be noted that slight capacitance can be observed also at the oxide of this specific wafer (the O line in the figure). Thus, this figure demonstrates the detection of charge trapping in a quantitative manner. Moreover, this analysis can be performed for each chemically resolved region. Time dependence of this process, as well as that of the discharge, can be followed by the same means.

Figure 7:
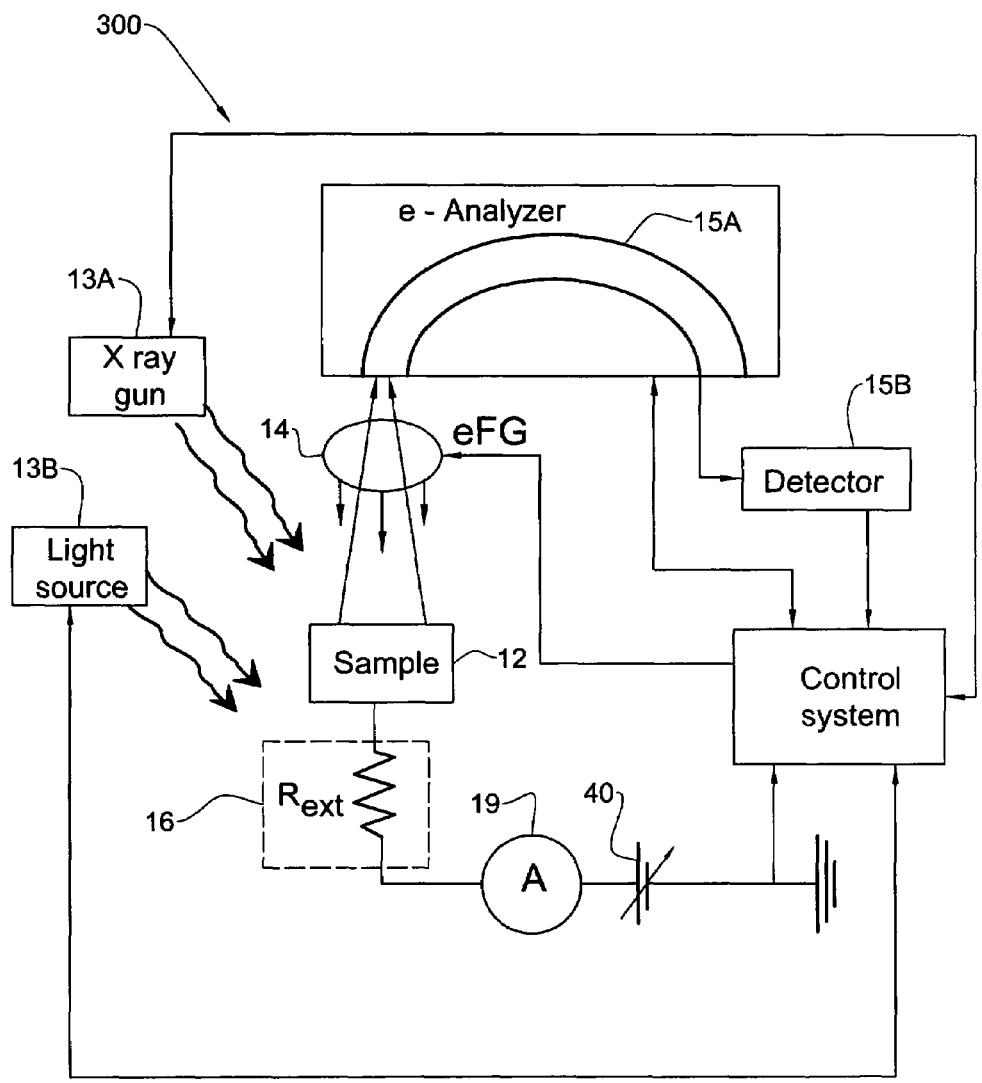
FIG. 7 illustrates a measurement device according to yet another embodiment of the present invention.
Figure 8A:
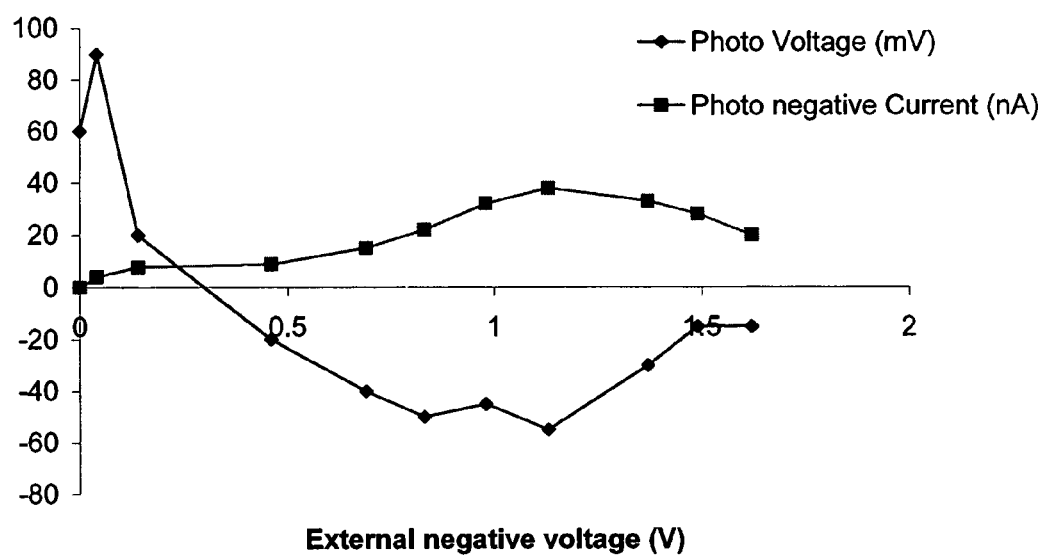
FIGS. 8A and 8B illustrate the experimental results of using the device of FIG. 7 for measuring the chemically resolved (here, by a Cd line) photo response of a sample.
Figure 8B:
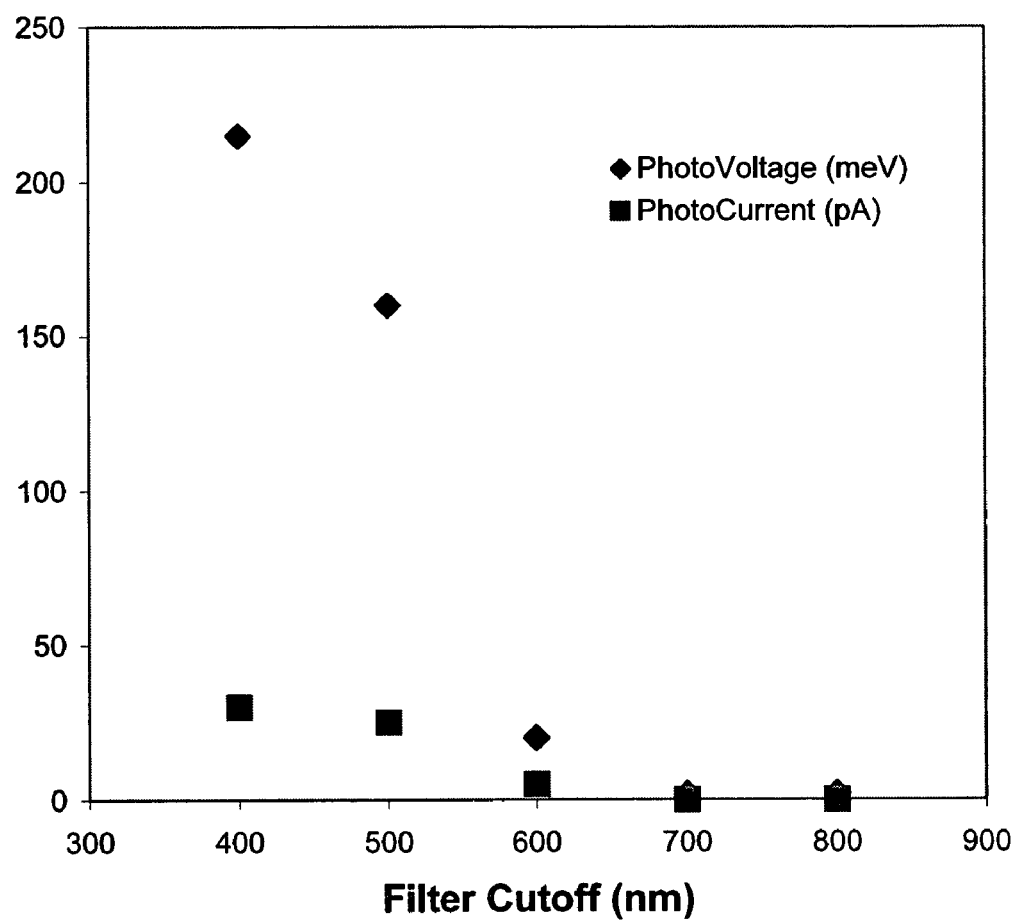

Reference is now made to FIGS. 7 and 8A–8B illustrating how the technique of the present invention can be used for photo voltage and photo current measurements.

FIG. 7 illustrates a measuring device 300 applied to a sample 12. The device comprises an excitation source 13 (e.g., X-ray beam source); an illuminator 313 (including one or more light sources); a power supply system which in the present example includes a charged particles' source 14 (electron flood gun) and preferably also includes a voltage supply unit 40; a detection system which in the present example includes an analyzer 15A (electron spectrometer), a detector 15B, and an ampermeter 19; and a control system 18.

FIG. 8A shows the (chemically resolved) photo response of the sample 12 including CdSe nanoparticles grown on a Si substrate. The external voltage is supplied by the eFG 14. The light used is a continuous halogen lamp. It should, however, be noted that the illumination system can include one or more lamps or lasers. The photovoltage is measured with the Cd signal. In the graphs, each data point corresponds to different eFG operating conditions (and hence different incoming electron gun flux). FIG. 8B illustrates wavelength dependence of the photo response of CdSe nanoparticles on Si, measured by using high-pass wavelength filters at the exit of the halogen lamp. The data corresponds to the lower wavelength cutoff values in the transmission of the filters.

Figure 9:
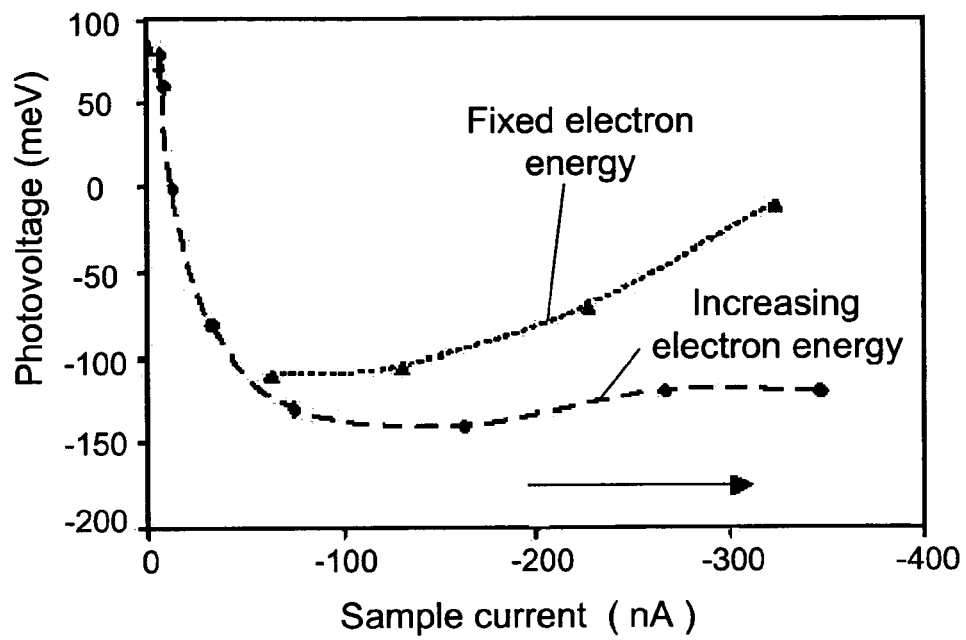
Figure 10:
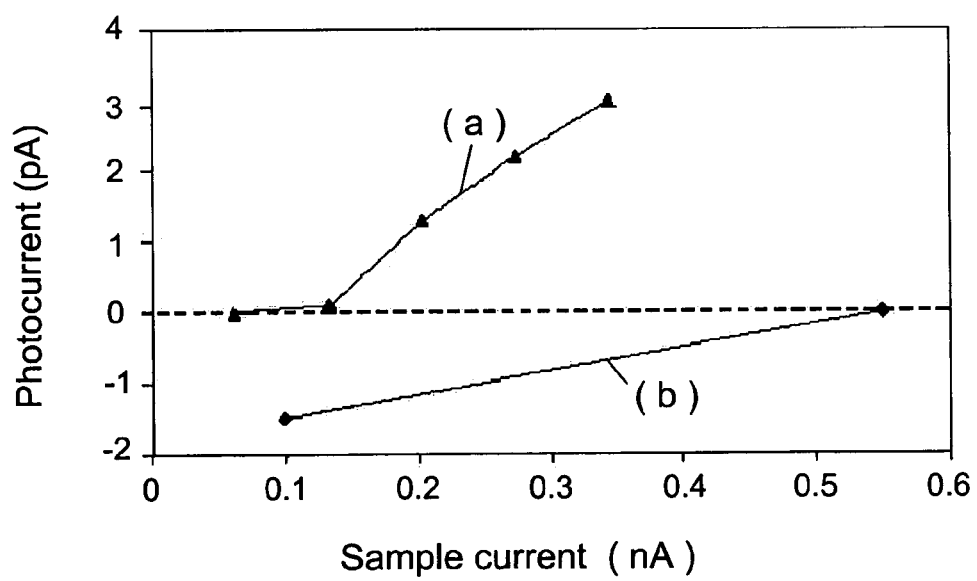

Reference is made to FIGS. 9 and 10 showing the experimental results of photovoltage measurements in CdSe films on Si, aimed at studying the effect of an external electrical signal on the photoresponse of nanocrystalline CdSe films.

FIG. 9 shows the photovoltage as a function of electric current through the sample of a p-type CdSe film on Si, for the cases of varying eFG electron energy and fixed eFG electron energy. Considering the case of increasing electron energy, the initially positive photovoltage (p-type) becomes smaller with increasing electron current and then changes to negative (n-type). This is reminiscent of the known effect of strong illumination and can be explained by saturation of electron traps in the $Cd(OH)_2$ leading to domination of the photoresponse by the holes in the CdSe. Furthermore, the small decrease in photovoltage at high electron currents, and stronger decrease at fixed electron energy, is consistent with a mechanism describing the negative differential resistance, observable in these samples: increasing electron current annihilates photogenerated holes. When the rate of this annihilation is slow relative to the photogeneration of holes, the photovoltage can reach high values. However, with increasing eFG flux, annihilation rates increase to values comparable with hole generation rates, and then saturation and even suppression of the photovoltage occurs. It is important to note that the higher energy (less interacting) electrons cause a smaller reduction of this photovoltage, due to the lower probability of their recombination with photogenerated holes.

FIG. 10 shows measurements of photocurrent (tungsten halogen illumination) as a function of total current, where the current is changed by the X-ray source power (no eFG input). In this case, power supply to the sample is varied by controlling the current of photoelectrons ejected from the sample by the X-ray source power. This feature is achieved by either varying the X-ray source power, or by the application of retarding (or accelerating) grid $V_G$, or by the application of bias voltage $V_B$ to the back contact of the sample. Two curves are shown, where curve (a) corresponds to a thin (ca. 10 nm) film which exhibits p-type behavior while curve (b) corresponds to a thick (ca. 50 nm) film which exhibits n-type behavior. It should be noted, although not specifically shown, that corresponding photovoltages are also positive for the p-type and negative for the n-type samples. Thus, the results from thin and thick films prove that thin films, dominated by the $Cd(OH)_2$ electron trapping behave as p-type and thick ones, dominated by CdSe hole trapping, as n-type.

The above experiments have thus shown that the phenomenon of a conductive type change in nanocrystalline CdSe films is due to relatively deep electron traps in the Cd(OH)2 which dominate the charge transport. Saturation of these traps by either light or an electron beam results in charge transport becoming dominated again by the CdSe hole traps (assumed to exist in higher concentration and therefore less readily saturated). Thus, in addition to chemical treatments, external parameters (light, electron-beam and X-ray beam) are shown to provide real time shaping of the potential profile in the film.

The technique of the present invention can provide detailed information on the photo response of the sample under controlled external fields. Redistribution of charges under illumination can be quantified by CREM, differentiating the different regions of the system, which is a unique capability of the present invention. In cells composed of regions with different photo activity, this capability is very important. The CREM of the present invention also provides for studying the role of contamination (or high concentration dopants) as traps of charges.

Those skilled in the art will readily appreciate that various modifications and changes can be applied to the embodiment of the invention as hereinbefore is described without departing from its scope defined in and by the appended claims. For example, although in the exemplified embodiment an XPS-based system is used, it should be understood that an AES is certainly an alternative tool for the same approach, proposing important advantages in its lateral resolution.

In the method claims that follow characters, which are used to designate claim steps, are provided for convenience only and do not apply any particular order of performing the steps.

The invention claimed is:

1. A method for measuring the electrical properties of a sample, the method comprising:
    (i) exciting the sample with high energy radiation to cause emission of internal charged particles from the sample;
    (ii) supplying electrical power to a circuit formed by the sample and any added component connected to a back contact of the sample, said supplying of electric power comprising at least one of the following: irradiating the sample by low energy charged particles, subjecting the sample to an external field affecting the flux of emitted internal charged particles, and supplying a bias voltage to the back contact of the sample;
    (iii) during the power supply to the sample, carrying out at least one of the following: measuring the emitted charged particles versus their energy, and measuring an electric current through the sample; thereby enabling determination of the electrical properties of the sample.

2. The method of claim 1, wherein the determined electrical properties include at least one of the following: spectrally resolved I–V characteristic of the sample; a work function characteristic of the sample; electric leakage or breakdown conditions of the sample; and accumulation of charge within at least one region of the sample.

3. The method of claim 1, wherein said excitation of the sample is carried out by exciting X-ray radiation to cause the emission of internal electrons.

4. The method of claim 1, wherein said excitation of the sample is carried out by an exciting electron beam to cause the emission of internal electrons.

5. The method of claim 1, wherein said excitation of the sample is carried out by electromagnetic radiation to cause the emission of internal electrons.

6. The method of claim 1, wherein said excitation of the sample is carried out by an exciting ion beam to cause the emission of internal ions or electrons.

7. The method of claim 1, wherein said supplying of the electrical power includes irradiating the sample with an electron beam.

8. The method of claim 7, wherein said electron beam has a kinetic energy substantially not exceeding 20 eV.

9. The method of claim 7, wherein said electron beam has a few electron-volts kinetic energy.

10. The method of claim 7, wherein said electron beam has a kinetic energy substantially not exceeding 10 eV.

11. The method of claim 7, wherein said electron beam has a kinetic energy of about 0–5 eV.

12. The method of claim 7, wherein said irradiating electron beam creates negative power supply to the sample.

13. The method of claim 1, wherein said supplying of the electrical power includes irradiating the sample with an ion beam for thereby creating a positive or negative voltage supply to the sample.

14. The method of claim 13, wherein said irradiating ion beam is $He^+$-beam.

15. The method of claim 1, wherein said analyzing of the emitted charged particles versus their energy and generating the measured data is carried out by a distant from the sample charged particles' spectrometer and a detector connected to the output of the spectrometer.

16. The method of claim 15, wherein said spectrometer is an electron spectrometer.

17. The method of claim 15, wherein the measured data is indicative of local potential values at different chemical entities of the sample.

18. The method of claim 1, wherein both the emitted charged particles versus their energy and the electric current through the sample are measured.

19. The method of claim 18, wherein the measured electrical properties include an I–V characteristic of the sample.

20. The method of claim 18, wherein the measured electrical properties include an I–V characteristic of at least some of the regions or domains or chemical entities in the sample.

21. The method of claim 1, wherein the electric power supply comprises the irradiation with low energy charged particles, and at least one of said application of the external field and the bias voltage.

22. The method of claim 21, wherein said determination of the electrical properties includes evaluation of a work function at selected portions of the sample.

23. The method of claim 18, wherein the electric power supply comprises the irradiation with low energy charged particles, and at least one of said application of the external field and the bias voltage.

24. The method of claim 23, wherein said determination of the electrical properties includes evaluation of a work function at selected portions of the sample.

25. The method of claim 1, comprising varying the electric power supply to the sample.

26. The method of claim 21, comprising varying the electric power supply to the sample.

27. The method of claim 21, comprising varying the bias voltage applied to the back contact of the sample.

28. The method of claim 21, wherein the application of the bias voltage to the back contact of the sample provides negative or positive bias to the sample.

29. The method of claim 1, comprising illuminating the sample.

30. The method of claim 29, wherein both the emitted charged particles versus their energy and the electric current through the sample are measured.

31. The method of claim 29, wherein the measured properties include photoresponse of the sample to the illumination applied onto the sample.

32. The method of claim 29, wherein the measured properties include a wavelength dependence of a photoresponse of the sample.

33. The method of claim 31, wherein the photoresponse includes at least one of a photo current or photo voltage of the sample.

34. The method of claim 30, wherein the measured properties include photoresponse of the sample to the illumination applied onto the sample.

35. The method of claim 30, wherein the measured properties include a wavelength dependence of a photoresponse of the sample.

36. The method of claim 31, wherein the photoresponse includes at least one of a photo current or photo voltage of the sample.

37. The method of claim 1, wherein the irradiation of the sample by the charged particles provides an alternating current supply or voltage supply to the sample.

38. The method of claim 21, wherein said measuring of the electrical properties includes monitoring at least one of the current leakage in the sample, the electrical breakdown of at least one region of the sample, and the accumulation of charge within at least one region of the sample indicative of at least one discharge channel in the sample.

39. The method of claim 18, wherein the electric power supply comprises the irradiation with low energy charged particles, and at least one of said application of the external field and the bias voltage.

40. The method of claim 18, wherein said measuring of the electrical properties includes monitoring at least one of the current leakage in the sample, the electrical breakdown of at least one region of the sample, and the accumulation of charge within at least one region of the sample indicative of at least one discharge channel in the sample.

41. The method of claim 1, wherein the electric power supply comprises the application of bias voltage to the back contact of the sample, said measuring of the electrical properties includes determination of at least one of the current leakage in the sample and the electrical breakdown of at least one region of the sample.

42. The method of claim 1, wherein the electric power supply comprises the application of bias voltage to the back contact of the sample, said measuring of the electrical properties includes measuring charge accumulation in at least one capacitive region of the sample.

43. A method for measuring the electrical properties of a sample, the method comprising:
(i) exciting the sample with high energy radiation to cause emission of internal charged particles from the sample;
(ii) supplying variable electrical power to a circuit formed by the sample and any added component connected to a back contact of the sample, said supplying of electric power comprising at least one of the following: irradiating the circuit by low energy charged particles, subjecting the circuit to an external field affecting the flux of emitted internal charged particles, and applying bias voltage to the back contact of the sample;
(iii) during the variable power supply to the sample, measuring an electric current through the sample, and measuring the emitted charged particles versus their energy thereby extracting local potential values at chemical entities of the sample, thereby enabling determination of spectrally resolved I–V characteristic of the sample.

44. A method for measuring the electrical properties of a sample, the method comprising:
(i) exciting the sample with high energy radiation to cause emission of internal charged particles from the sample;
(ii) supplying variable electrical power to a circuit formed by the sample and any added component connected to a back contact of the sample, said supplying of electric power comprising at least one of the following: irradiating the circuit by low energy charged particles, subjecting the circuit to an external field affecting the flux of emitted internal charged particles, and applying bias voltage to the back contact of the sample;
(iii) during the variable power supply to the sample, measuring the emitted charged particles versus their energy thereby extracting local potential values at chemical entities of the sample, thereby enabling determination of spectrally resolved I–V characteristic of the sample.

45. A method for measuring the electrical properties of a sample, the method comprising:
(i) exciting the sample with high energy radiation to cause emission of internal charged particles from the sample;
(ii) supplying electrical power to a circuit formed by the sample and any added component connected to a back contact of the sample, said supplying of electric power comprising irradiating the sample by low energy charged particles, and carrying out at least one of the following: supplying a bias voltage to the back contact of the sample, and subjecting the sample to an external field affecting the flux of emitted internal charged particles;

(iii) during the electric power supply to the sample, measuring the emitted charged particles versus their energy, and thereby extracting local potential values at chemical entities of the sample and enabling evaluation of a work function characteristic of the sample.

46. A method for measuring the electrical properties of a sample, the method comprising:
   (i) exciting the sample with high energy radiation to cause emission of internal charged particles from the sample;
   (ii) supplying electrical power to a circuit formed by the sample and any added component connected to a back contact of the sample, said supplying of electric power comprising irradiating the sample by low energy charged particles, and carrying out at least one of the following: supplying a bias voltage to the back contact of the sample, and subjecting the sample to an external field affecting the flux of emitted internal charged particles;
   (iii) during the electric power supply to the sample, measuring an electric current through the sample and measuring the emitted charged particles versus their energy, and thereby extracting local potential values at chemical entities of the sample and enabling evaluation of a work function characteristic of the sample.

47. A method for measuring the electrical properties of a sample, the method comprising:
   (i) exciting the sample with high energy radiation to cause emission of internal charged particles from the sample;
   (ii) supplying electrical power to a circuit formed by the sample and any added component connected to a back contact of the sample, said supplying of electric power comprising at least one of the following: irradiating the sample by low energy charged particles, applying bias voltage to the back contact of the sample, and subjecting the circuit to an external field affecting the flux of emitted internal charged particles;
   (iii) during the electric power supply, measuring the emitted charged particles versus their energy thereby extracting local potential values at chemical entities of the sample, thereby enabling characterization of electric leakage or breakdown conditions of the sample.

48. A method for measuring the electrical properties of a sample, the method comprising:
   (i) exciting the sample with high energy radiation to cause emission of internal charged particles from the sample;
   (ii) supplying electrical power to a circuit formed by the sample and any added component connected to a back contact of the sample, said supplying of electric power comprising irradiating the sample by low energy charged particles, and applying bias voltage to the back contact of the sample;
   (iii) during the electric power supply, measuring the emitted charged particles versus their energy thereby extracting local potential values at chemical entities of the sample, thereby enabling characterization of electric leakage or breakdown conditions of the sample.

49. A method for measuring the electrical properties of a sample, the method comprising:
   (i) exciting the sample with high energy radiation to cause emission of internal charged particles from the sample;
   (ii) supplying electrical power to a circuit formed by the sample and any added component connected to a back contact of the sample, said supplying of electric power comprising at least one of the following: irradiating the circuit by low energy charged particles, applying bias voltage to the back contact of the sample, and subjecting the circuit to an external field affecting the flux of emitted internal charged particles;
   (iii) during the power supply to the sample, measuring the emitted charged particles versus their energy thereby extracting local potential values at chemical entities of the sample; thereby enabling characterization of accumulation of charge within at least one region of the sample.

50. A method for measuring the electrical properties of a sample, the method comprising:
   (i) exciting the sample with high energy radiation to cause emission of internal charged particles from the sample;
   (ii) supplying electrical power to a circuit formed by the sample and any added component connected to a back contact of the sample, said supplying of electric power comprising irradiating the circuit by low energy charged particles, and applying bias voltage to the back contact of the sample;
   (iii) during the power supply to the sample, measuring the emitted charged particles versus their energy thereby extracting local potential values at chemical entities of the sample; thereby enabling characterization of accumulation of charge within at least one region of the sample.

51. A method for measuring the electrical properties of a sample, the method comprising:
   (i) exciting the sample with high energy radiation to cause emission of internal charged particles from the sample;
   (ii) supplying electrical power to a circuit formed by the sample and any added component connected to a back contact of the sample, said supplying of electric power comprising at least one of the following: irradiating the circuit by low energy charged particles, subjecting the circuit to an external field affecting the flux of emitted internal charged particles, and supplying a bias voltage to the back contact of the sample;
   (iii) affecting the sample by external electromagnetic radiation;
   (iv) during the power supply to the sample and illumination of the sample, measuring the emitted charged particles versus their energy thereby extracting local potential values at chemical entities of the sample; thereby enabling determination of at least one of photo voltage and photo current of the sample.

52. A device for use in measuring electrical properties of a sample, the device comprising:
   (a) an excitation source configured and operable to generate high energy radiation to be applied to the sample to cause emission of internal charged particles from the sample;
   (b) an electric power supply system associated with a circuit formed by the sample and any added component connected to a back contact of the sample, said electric power supply system comprising at least one of the following: a source of charged particles operable to irradiate the sample with a beam of low energy charged particles; a source of an external field affecting the flux of the emitted charged particles; and a voltage supply unit operable to supply bias voltage to the back contact of the sample; and
   (c) a detection system including at least one of the following: a voltmeter for accommodating at a distance from the sample and comprising a charged particles' spectrometer for contactless detecting and analyzing the emitted charged particles versus their energy, and thus extracting local potentials of different chemical entities in the sample and generating measured data indicative thereof; and an ampermeter for measuring an electric current through the sample;

the device being thereby operable for providing at least one of the following: determination of spectrally resolved I–V characteristic of the sample; evaluation of a work function characteristic of the sample; characterization of electric leakage or breakdown conditions of the sample; and characterization of accumulation of charge within at least one region of the sample.

53. The device of claim 52, wherein said excitation source includes an X-ray beam source to cause the emission of internal electrons.

54. The device of claim 52, wherein said excitation source includes an electron beam source to cause the emission of internal electrons.

55. The device of claim 52, wherein said excitation source includes a source of electromagnetic radiation to cause the emission of internal electrons.

56. The device of claim 52, wherein said excitation source includes an ion beam source to cause the emission of ions.

57. The device of claim 52, also comprising an illumination assembly operable to affect the sample by external illumination.

58. The device of claim 52, wherein said source of charged particles includes an electron flood gun.

59. The device of claim 58, wherein an electron beam generated by the electron beam source has a kinetic energy substantially not exceeding 20 eV.

60. The device of claim 58, wherein an electron beam generated by the electron beam source has a few electron-volts kinetic energy.

61. The device of claim 58, wherein an electron beam generated by the electron beam source has a kinetic energy substantially not exceeding 10 eV.

62. The device of claim 58, wherein an electron beam generated by the electron beam source has a kinetic energy of about 0–5 eV.

63. The device of claim 52, wherein said source of charged particles includes an ion beam source.

64. The device of claim 52, wherein said voltage supply unit is configured and operable to apply one or more back bias voltages to the sample.

65. The device of claim 57, configured and operable to measure at least one of the following: a photoresponse of the sample to the illumination applied onto the sample; and wavelength dependence of a photoresponse of the sample.

66. A device for use in measuring electrical properties of a sample, the device comprising:
 (a) an excitation source configured and operable to generate high energy radiation to be applied to the sample to cause emission of internal charged particles from the sample;
 (b) an electric power supply system associated with a circuit formed by the sample and any added component connected to a back contact of the sample, said electric power supply system comprising at least one of the following: a source of charged particles operable to irradiate the sample with a low energy charged particles' beam, a source of external field for affecting the flux of the emitted charged particles, and a voltage supply unit for supplying bias voltage to the back contact of the sample;
 (c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;

the device being therefore operable for determining a spectrally resolved I–V characteristic of the sample.

67. A device for use in measuring electrical properties of a sample, the device comprising:
 (a) an excitation source configured and operable to generate high energy radiation to be applied to the sample to cause emission of internal charged particles from the sample;
 (b) an electric power supply system associated with a circuit formed by the sample and any added component connected to a back contact of the sample, said electric power supply system comprising at least one of the following: a source of charged particles operable to irradiate the sample with a low energy charged particles' beam, a source of external field for affecting the flux of the emitted charged particles, and a voltage supply unit for supplying bias voltage to the back contact of the sample;
 (c) a detection system including: a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof, and at least one ampermeter for measuring an electric current through the sample;

the device being therefore operable for determining a spectrally resolved I–V characteristic of the sample.

68. A device for use in measuring electrical properties of a sample, the device comprising:
 (a) an excitation source configured and operable to generate high energy radiation to be applied to the sample to cause emission of internal charged particles from the sample;
 (b) an illumination assembly operable to affect the sample by external electromagnetic radiation;
 (c) an electric power supply system associated with a circuit formed by the sample and any added component connected to a back contact of the sample, said electric power supply system comprising at least one of the following: a source of charged particles operable to irradiate the sample with a low energy charged particles' beam, a source of external field for affecting the flux of emitted charged particles, and a voltage supply unit for supplying bias voltage to the back contact of the sample;
 (d) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof; and the device being therefore operable for determining at least one of photo voltage and photo current of the sample.

69. A device for use in measuring electrical properties of a sample, the device comprising:
(a) an excitation source configured and operable to generate high energy radiation to be applied to the sample to cause emission of internal charged particles from the sample;
(b) an illumination assembly operable to affect the sample by external electromagnetic radiation;
(c) an electric power supply system associated with a circuit formed by the sample and any added component connected to a back contact of the sample, said electric power supply system comprising at least one of the following: a source of charged particles operable to irradiate the sample with a low energy charged particles' beam, a source of external field for affecting the flux of emitted charged particles, and a voltage supply unit for supplying bias voltage to the back contact of the sample;
(d) a detection system including: a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof; and at least one ampermeter for measuring an electric current through the sample;
the device being therefore operable for determining at least one of photo voltage and photo current of the sample.

70. A device for use in measuring electrical properties of a sample, the device comprising:
(a) an excitation source configured and operable to generate high energy radiation to be applied to the sample to cause emission of internal charged particles from the sample;
(b) an electric power supply system associated with a circuit formed by the sample and any added component connected to a back contact of the sample, said electric power supply system comprising a source of charged particles operable to irradiate the sample with a low energy charged particles' beam, and at least one of the following: a voltage supply unit for supplying bias voltage to the back contact of the sample, and a source of external field for affecting the flux of the emitted charged particles;
(c) a detection system including: a voltmeter for accommodating at a distance from the circuit and comprising a charged particles' spectrometer for contactless detecting and analyzing the emitted charged particles versus their energy and therefore extracting local potentials of different chemical entities in the sample, and generating measured data indicative thereof;
the device being therefore operable for evaluating a work function of the sample.

71. A device for use in measuring electrical properties of a sample, the device comprising:
(a) an excitation source configured and operable to generate high energy radiation to be applied to the sample to cause emission of internal charged particles from the sample;
(b) an electric power supply system associated with a circuit formed by the sample and any added component connected to a back contact of the sample, said electric power supply system comprising a source of charged particles operable to irradiate the sample with a low energy charged particles' beam, and at least one of the following: a voltage supply unit for supplying bias voltage to the back contact of the sample, and a source of external field for affecting the flux of the emitted charged particles;
(c) a detection system including: a voltmeter for accommodating at a distance from the circuit and comprising a charged particles' spectrometer for contactless detecting and analyzing the emitted charged particles versus their energy and therefore extracting local potentials of different chemical entities in the sample, and generating measured data indicative thereof; and at least one ampermeter for measuring an electric current through the sample;
the device being therefore operable for evaluating a work function of the sample.

72. A device for use in measuring electrical properties of a sample, the device comprising:
(a) an excitation source configured and operable to generate high energy radiation to be applied to the sample to cause emission of internal charged particles from the sample;
(b) an electric power supply system associated with a circuit formed by the sample and any added component connected to a back contact of the sample, said electric power supply system comprising a source of charged particles operable to irradiate the sample with a low energy charged particles' beam, and at least one of the following: a voltage supply unit for supplying bias voltage to the back contact of the sample, and a source of external field for affecting the flux of the emitted charged particles; and
(c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;
the device being therefore operable for providing characterization of electric leakage or breakdown conditions of the sample.

73. A device for use in measuring electrical properties of a sample, the device comprising:
(a) an excitation source configured and operable to generate high energy radiation to be applied to the sample to cause emission of internal charged particles from the sample;
(b) an electric power supply system associated with a circuit formed by the sample and any added component connected to a back contact of the sample, said electric power supply system comprising a source of charged particles operable to irradiate the sample with a low energy charged particles' beam, and a voltage supply unit for supplying bias voltage to the back contact of the sample; and
(c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;
the device being therefore operable for providing characterization of electric leakage or breakdown conditions of the sample.

74. A device for use in measuring electrical properties of a sample, the device comprising:
  (a) an excitation source configured and operable to generate high energy radiation to be applied to the sample to cause emission of internal charged particles from the sample;
  (b) an electric power supply system associated with a circuit formed by the sample and any added component connected to a back contact of the sample, said electric power supply system comprising a source of charged particles operable to irradiate the sample with a low energy charged particles' beam, and at least one of the following: a voltage supply unit for supplying bias voltage to the back contact of the sample, and a source of external field for affecting the flux of the emitted charged particles; and
  (c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;
  the device being therefore operable for providing characterization of accumulation of charge within at least one region of the sample.

75. A device for use in measuring electrical properties of a sample, the device comprising:
  (a) an excitation source configured and operable to generate high energy radiation to be applied to the sample to cause emission of internal charged particles from the sample;
  (b) an electric power supply system associated with a circuit formed by the sample and any added component connected to a back contact of the sample, said electric power supply system comprising a source of charged particles operable to irradiate the sample with a low energy charged particles' beam, and a voltage supply unit for supplying bias voltage to the back contact of the sample; and
  (c) a detection system including a voltmeter for accommodating at a distance from the sample and comprising a charged particles' spectrometer for contactless detecting and analyzing the emitted charged particles versus their energy and therefore extracting local potentials of different chemical entities in the sample, and generating measured data indicative thereof;
  the device being therefore operable for providing characterization of accumulation of charge within at least one region of the sample.

* * * * *